(12) United States Patent
Sadda et al.

(10) Patent No.: US 11,452,443 B2
(45) Date of Patent: *Sep. 27, 2022

(54) SYSTEMS, METHODS, AND DEVICES FOR OPTICAL COHERENCE TOMOGRAPHY MULTIPLE ENFACE ANGIOGRAPHY AVERAGING

(71) Applicant: Doheny Eye Institute, Los Angeles, CA (US)

(72) Inventors: SriniVas R. Sadda, Pasadena, CA (US); Akihito Uji, Kyoto (JP)

(73) Assignee: Doheny Eye Institute, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/145,872

(22) Filed: Jan. 11, 2021

(65) Prior Publication Data

US 2021/0204808 A1 Jul. 8, 2021

Related U.S. Application Data

(63) Continuation of application No. 16/575,212, filed on Sep. 18, 2019, now Pat. No. 10,918,274, which is a
(Continued)

(51) Int. Cl.
*A61B 3/00* (2006.01)
*A61B 3/10* (2006.01)
(Continued)

(52) U.S. Cl.
CPC ............ *A61B 3/102* (2013.01); *A61B 3/0041* (2013.01); *A61B 3/0058* (2013.01);
(Continued)

(58) Field of Classification Search
CPC ..... A61B 3/102; A61B 3/0041; A61B 3/0058; A61B 3/1241; G06T 5/003; G06T 5/50;
(Continued)

(56) References Cited

U.S. PATENT DOCUMENTS

| 4,109,653 A | 8/1978 | Kozam et al. |
| 4,381,778 A | 5/1983 | Kozam et al. |

(Continued)

FOREIGN PATENT DOCUMENTS

| CN | 103810709 A | 5/2014 |
| CN | 103854284 A | 6/2014 |

(Continued)

OTHER PUBLICATIONS

Extended European Search Report dated Jul. 3, 2019 in European Application No. 16860729.9, in 9 pages.
(Continued)

*Primary Examiner* — Aaron W Carter
(74) *Attorney, Agent, or Firm* — Knobbe, Martens, Olson & Bear, LLP

(57) ABSTRACT

The disclosure herein provides methods, systems, and devices for improving optical coherence tomography machine outputs through multiple enface optical coherence tomography angiography averaging techniques. The embodiments disclosed herein can be utilized in ophthalmology for employing optical coherence tomography (OCT) for in vivo visualization of blood vessels and the flow of blood in an eye of a patient, which is also known generally as optical coherence tomography angiography (OCTA). The embodiments disclosed herein can use linear registration, affine registration and/or elastic registration to align a plurality of optical coherence tomography angiography images or videos at corresponding superficial vascular layers having well-defined features or landmarks, and to apply the same linear registration, affine registration and/or elastic registration settings and/or data to corresponding deeper tissue layers, such as the choriocapillaris, which generally do not have well-defined features or landmarks, in order to align a plurality of corresponding deeper tissue layers for the purpose of (Continued)

pose of averaging the images or video to produce a clearer and more accurate image or video of the tissue structure at deeper tissue layers.

20 Claims, 19 Drawing Sheets

Related U.S. Application Data continuation of application No. 15/992,028, filed on May 29, 2018, now Pat. No. 10,456,031, which is a continuation of application No. 15/927,966, filed on Mar. 21, 2018, now Pat. No. 10,010,249.

(60) Provisional application No. 62/505,355, filed on May 12, 2017, provisional application No. 62/475,743, filed on Mar. 23, 2017.

(51) Int. Cl.
*A61B 3/12* (2006.01)
*G06T 7/30* (2017.01)
*G06T 7/00* (2017.01)
*G06T 7/33* (2017.01)
*G06T 5/50* (2006.01)
*G06T 5/00* (2006.01)

(52) U.S. Cl.
CPC ............ *A61B 3/1241* (2013.01); *G06T 5/003* (2013.01); *G06T 5/50* (2013.01); *G06T 7/0012* (2013.01); *G06T 7/30* (2017.01); *G06T 7/33* (2017.01); *G06T 2207/10101* (2013.01); *G06T 2207/30041* (2013.01)

(58) Field of Classification Search
CPC ........... G06T 7/0012; G06T 7/30; G06T 7/33; G06T 2207/10101; G06T 2207/30041
See application file for complete search history.

(56) References Cited

U.S. PATENT DOCUMENTS

| | | | |
|---|---|---|---|
| 4,387,707 A | 6/1983 | Polikoff | |
| 4,564,016 A | 1/1986 | Maurice et al. | |
| 6,024,095 A | 2/2000 | Stanley, III | |
| 6,154,671 A | 11/2000 | Parel et al. | |
| 6,319,240 B1 | 11/2001 | Beck | |
| 6,918,904 B1 | 7/2005 | Peyman | |
| 9,408,532 B2 | 8/2016 | Makihira | |
| 9,483,866 B2 | 11/2016 | Stetson | |
| 10,010,249 B1 | 7/2018 | Sadda et al. | |
| 10,117,776 B2 | 11/2018 | Tan | |
| 10,441,164 B1 | 10/2019 | De Sisternes et al. | |
| 10,456,031 B2 | 10/2019 | Sadda et al. | |
| 10,529,061 B2 | 1/2020 | Wang et al. | |
| 10,918,274 B2* | 2/2021 | Sadda ..................... A61B 3/102 |
| 2002/0147424 A1 | 10/2002 | Ostrow et al. | |
| 2004/0193097 A1 | 9/2004 | Hofmann et al. | |
| 2007/0115481 A1 | 5/2007 | Toth et al. | |
| 2007/0129693 A1 | 6/2007 | Hunter et al. | |
| 2007/0282405 A1 | 12/2007 | Wong, Jr. et al. | |
| 2008/0183123 A1 | 7/2008 | Behar-Cohen | |
| 2011/0007957 A1 | 1/2011 | Sakagawa | |
| 2012/0078162 A1 | 3/2012 | Gibson | |
| 2012/0274783 A1 | 11/2012 | Ko et al. | |
| 2012/0288175 A1 | 11/2012 | Iwase et al. | |
| 2013/0039557 A1 | 2/2013 | Wei et al. | |
| 2014/0228681 A1 | 8/2014 | Jia et al. | |
| 2014/0270436 A1 | 9/2014 | Dascal et al. | |
| 2014/0309613 A1 | 10/2014 | Behar-Cohen et al. | |
| 2014/0316326 A1 | 12/2014 | Behar-Cohen | |
| 2015/0159992 A1 | 6/2015 | Buckland et al. | |
| 2016/0183786 A1 | 6/2016 | Wei et al. | |
| 2016/0227999 A1 | 8/2016 | An et al. | |
| 2016/0228000 A1 | 8/2016 | Spaide | |
| 2016/0317026 A1 | 11/2016 | Ringler et al. | |
| 2016/0331229 A1 | 11/2016 | Huang et al. | |
| 2017/0020387 A1 | 1/2017 | Ringler et al. | |
| 2017/0035286 A1 | 2/2017 | Meyer et al. | |
| 2017/0119580 A1 | 5/2017 | Tan | |
| 2017/0164825 A1 | 6/2017 | Chen et al. | |
| 2017/0169590 A1 | 6/2017 | Huang et al. | |
| 2017/0258321 A1 | 9/2017 | Dastmalchi et al. | |
| 2017/0296293 A1 | 10/2017 | Mak et al. | |
| 2018/0020909 A1 | 1/2018 | Jia et al. | |
| 2018/0049635 A1 | 2/2018 | Uji et al. | |
| 2018/0055355 A1 | 3/2018 | Sarunic et al. | |
| 2018/0153396 A1 | 6/2018 | Uchida | |
| 2018/0182082 A1 | 6/2018 | Jia et al. | |
| 2018/0232864 A1 | 8/2018 | Wang et al. | |
| 2018/0256024 A1 | 9/2018 | An et al. | |
| 2018/0260952 A1 | 9/2018 | Bagherinia et al. | |
| 2018/0317851 A1 | 11/2018 | Jia et al. | |
| 2018/0353064 A1 | 12/2018 | Soetikno et al. | |
| 2019/0000313 A1 | 1/2019 | Sadda et al. | |
| 2019/0073758 A1 | 3/2019 | Iwase et al. | |
| 2019/0073779 A1 | 3/2019 | Iwase et al. | |
| 2019/0073780 A1 | 3/2019 | Iwase et al. | |
| 2019/0083312 A1 | 3/2019 | Tan | |
| 2019/0150729 A1 | 5/2019 | Huang et al. | |
| 2020/0077887 A1* | 3/2020 | Sadda ..................... G06T 7/30 |
| 2021/0204808 A1* | 7/2021 | Sadda ..................... G06T 7/33 |

FOREIGN PATENT DOCUMENTS

| | | |
|---|---|---|
| EP | 2 266 656 A2 | 12/2010 |
| EP | 3 367 982 | 9/2018 |
| JP | 2016-198279 A | 12/2016 |
| WO | WO 2009/128912 | 10/2009 |
| WO | WO 2011/155150 | 12/2011 |
| WO | WO 2014/085911 | 6/2014 |
| WO | WO 2015/195048 | 12/2015 |
| WO | WO 2017/075105 | 5/2017 |

OTHER PUBLICATIONS

Fan, Bao Jian et al., DNA sequence variants in the LOXL1 gene are associated with pseudoexfoliation glaucoma in a U.S. clinic-based population with broad ethnic diversity, BMC Medical Genetics, 2008, vol. 9, No. 1, 1 (internal pp. 1-7). See pp. 1-6.
International Preliminary Report on Patentability and Written Opinion dated May 11, 2018 for International Application No. PCT/US2016/058949, in 15 pages.
International Search Report and Written Opinion dated Jan. 17, 2017 for International Application No. PCT/US2016/058949, in 20 pages.
International Search Report and Written Opinion dated Aug. 3, 2018 for International Application No. PCT/US2018/023653, in 11 pages.
Liu, Xuyang et al., Gene therapy targeting glaucoma: where are we?, Survey of Ophthalmology, 2009, vol. 54, Issue 4, pp. 472-486. See pp. 472-482.
Touchard et al.: "The ciliary smooth muscle electrotransfer: basic principles and potential for sustained intraocular production of therapeutic proteins", The Journal of Gene Medicine, vol. 12, 11, Nov. 1, 2010 (Nov. 1, 2010), pp. 904-919, Xp055211787, ISSN: 1099-498X, DOI: 10.1002/jgm. 1517.
Extended European Search Report dated Nov. 16, 2020 in European Application No. 18772477.8, in 7 pages.
Office Action issued in Japanese Application No. 2019-552116 dated Feb. 22, 2022.

* cited by examiner

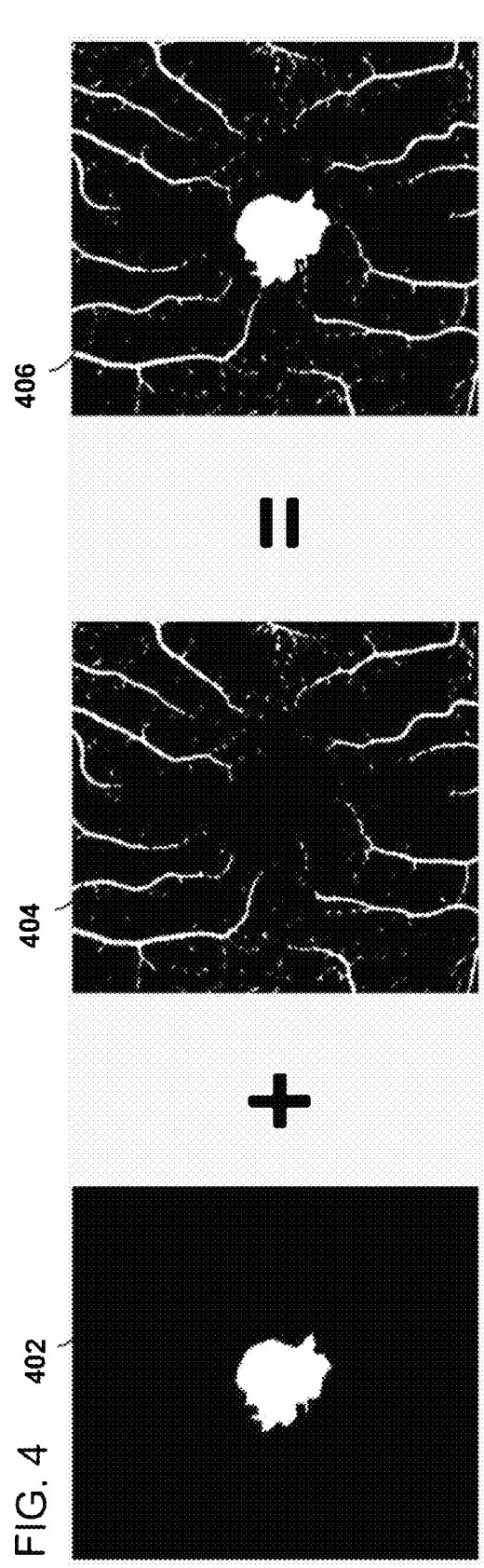

TABLE 1. Differences in morphological parameters of the choriocapillaris among 9 scans

| | ICC | CV (%) |
|---|---|---|
| Number of flow voids | 0.944 | 7.14 |
| Total flow voids area | 0.999 | 3.47 |
| Average size of the flow voids | 0.928 | 10.85 |
| Circularity of the flow voids | 0.856 | 2.02 |
| Vessel density | 0.926 | 2.16 |
| Vessel length density | 0.938 | 1.51 |
| Vessel diameter index | 0.882 | 1.09 |

Difference in flow voids area (mm$^2$); 1.79 ± 0.05 (1.71 ~ 1.90)
Difference in flow voids area (%); 42.2 ± 1.3

FIG. 11

TABLE 2. Differences in the morphological parameters of the choriocapillaris between single image and averaged image in optical coherence tomographic angiography imaging.

| | Single image | | Averaged image | P value |
|---|---|---|---|---|
| Number of flow voids | 1254 ± 219 | < | 1423 ± 248 | <0.0001 |
| Total flow voids area (mm²) | 1.61 ± 0.11 | > | 1.25 ± 0.18 | <0.0001 |
| Total flow voids area (%) | 38.1 ± 3.0 | > | 29.6 ± 4.5 | <0.0001 |
| Average size of the flow voids (μm²) | 1364 ± 367 | > | 911 ± 311 | <0.0001 |
| Circularity of the flow voids | 0.61 ± 0.02 | < | 0.68 ± 0.03 | <0.0001 |
| Vessel density (%) | 61.9 ± 3.0 | < | 70.7 ± 4.5 | <0.0001 |
| Vessel length density (%) | 10.2 ± 0.4 | | 10.3 ± 0.5 | 0.0997 |
| Vessel diameter index | 6.06 ± 0.12 | < | 6.85 ± 0.26 | <0.0001 |

SD = standard deviation

SYSTEMS, METHODS, AND DEVICES FOR OPTICAL COHERENCE TOMOGRAPHY MULTIPLE ENFACE ANGIOGRAPHY AVERAGING

CROSS-REFERENCE TO RELATED APPLICATIONS

This application is a continuation of U.S. patent application Ser. No. 16/575,212, filed Sep. 18, 2019, titled "SYSTEMS, METHODS, AND DEVICES FOR OPTICAL COHERENCE TOMOGRAPHY MULTIPLE ENFACE ANGIOGRAPHY AVERAGING", which is a continuation of U.S. patent application Ser. No. 15/992,028, filed May 29, 2018 and issued on Oct. 29, 2019 as U.S. Pat. No. 10,456,031, titled "SYSTEMS, METHODS, AND DEVICES FOR OPTICAL COHERENCE TOMOGRAPHY MULTIPLE ENFACE ANGIOGRAPHY AVERAGING," which is a continuation of U.S. application Ser. No. 15/927,966, filed Mar. 21, 2018 and issued on Jul. 3, 2018 as U.S. Pat. No. 10,010,249, titled "SYSTEMS, METHODS, AND DEVICES FOR OPTICAL COHERENCE TOMOGRAPHY MULTIPLE ENFACE ANGIOGRAPHY AVERAGING", which claims the benefit under 35 U.S.C. 119(c) to U.S. Provisional Patent Application No. 62/475,743 filed Mar. 23, 2017, titled "SYSTEMS, METHODS AND DEVICES FOR ENHANCED IMAGING USING MULTIPLE ENFACE OPTICAL COHERENCE TOMOGRAPHY ANGIOGRAPHY IMAGE AVERAGING," and to U.S. Provisional Patent Application No. 62/505,355 filed May 12, 2017, titled "SYSTEMS, METHODS, AND DEVICES FOR OPTICAL COHERENCE TOMOGRAPHY MULTIPLE ENFACE ANGIOGRAPHY AVERAGING," the entirety of each of the foregoing applications is hereby incorporated herein by reference under 37 CFR 1.57. Any and all applications for which a foreign or domestic priority claim is identified in the Application Data Sheet as filed with the present application are hereby incorporated by reference under 37 C.F.R. § 1.57.

BACKGROUND

Field

The embodiments of the disclosure generally relate to optical coherence tomography, and more particularly to systems, devices, and methods for improving optical coherence tomography machine outputs through multiple enface optical coherence tomography angiography averaging techniques.

Description

With the development of optical coherence tomography technology, doctors can obtain three-dimensional images of biological tissue. In many instances, such optical coherence tomography medical images are generated with micrometer-resolution. For example, ophthalmologists can observe biological tissue in the back of the eye without conducting an invasive surgical procedure. Such observations of posterior eye tissue can allow ophthalmologists to view tissue relatively deeply below the surface because optical coherence tomography generally utilizes low-coherence interferometry, and in some instances, employing near-infrared light. This use of relatively long wavelength light allows the light generated from optical coherence tomography machines to penetrate deeply into the tissue, which is the scattering medium. However, as compared to other optical techniques, such as confocal microscopy, the images generated from optical coherence tomography machines can often have less resolution and/or appear less than clear and/or are blurry due to various issues.

SUMMARY

Various embodiments described herein relate to systems, methods, and devices for obtaining and processing images of a biological material.

In some embodiments, a system for obtaining and processing images of a biological material as disclosed herein can comprise: an optical coherence tomography (OCT) scanner configured to generate a plurality of OCT images; one or more computer readable storage devices configured to store a plurality of computer executable instructions; and one or more hardware computer processors in communication with the one or more computer readable storage devices and configured to execute the plurality of computer executable instructions in order to cause the system to: access, from the OCT scanner, the plurality of OCT images; generate, from the plurality of OCT images, a plurality of enface images of one or more superficial layers of the biological material and a plurality of enface images of one or more deep layers of the biological material; apply one or more image registration techniques to the plurality of enface images of the one or more superficial layers to produce image alignment settings; store the image alignment settings; generate at least one averaged enface image of each of the one or more deep layers by applying one or more image registration techniques, based at least in part on the stored image alignment settings, to the plurality of enface images of the one or more deep layers; and output the one or more averaged enface images.

In certain embodiments, the image registration techniques can comprise at least one of linear registration, affine registration, and elastic registration. In certain embodiments, the system is further caused to divide each of the plurality of enface images of the one or more superficial layers and each of the plurality of enface images of the one or more deep layers into a plurality of sectors, and wherein the system is further caused to apply registration to each of the plurality of sectors individually. In certain embodiments, the biological material comprises retinal, choroid, or another eye tissue. In certain embodiments, the one or more superficial layers comprise at least a superficial vascular plexus. In certain embodiments, the one or more deep layers comprise at least one of a choriocapillaris and deep capillary plexus. In certain embodiments, the plurality of OCT images comprise optical coherence tomography angiography (OCTA) images. In certain embodiments, the system is configured to align the plurality of OCT images in a three-dimensional coordinate space. In certain embodiments, the system is configured to account for movement of the biological material during generation of the plurality of OCT images by the OCT scanner. In certain embodiments, the movement comprises at least one of translational movement and rotational movement. In certain embodiments, the one or more superficial layers comprise well-defined features or landmarks. In certain embodiments, the well-defined features or landmarks comprise blood vessels.

In some embodiments, a system for obtaining and processing images of a biological material as disclosed herein can comprise: one or more computer readable storage devices configured to store a plurality of computer executable instructions; and one or more hardware computer processors in communication with the one or more computer readable storage devices and configured to execute the plurality of computer executable instructions in order to cause the system to: access or obtain a plurality of OCT images generated from an OCT scanner; generate, from the plurality of OCT images, a plurality of enface images of one or more superficial layers of the biological material and a plurality of enface images of one or more deep layers; apply one or more image registration techniques to the plurality of enface images of the one or more superficial layers to generate one or more image alignment settings; generate an averaged enface image of each of the one or more deep layers by applying one or more image registration techniques, based at least in part on the one or more generated image alignment settings, to the plurality of enface images of the one or more deep layers; and transmit the one or more averaged enface images for causing display of the one or more averaged enface images by an output device.

In certain embodiments, the image registration techniques comprise at least one of linear registration, affine registration, and elastic registration. In certain embodiments, the system is further caused to divide each of the plurality of enface images of the one or more superficial layers and each of the plurality of enface images of the one or more deep layers into a plurality of sectors, and wherein the system is further caused to apply registration to each of the plurality of sectors individually. In certain embodiments, the biological material comprises retinal, choroid, or another eye tissue. In certain embodiments, the one or more superficial layers comprise at least a superficial vascular plexus. In certain embodiments, the one or more deep layers comprise at least one of a choriocapillaris and deep capillary plexus. In certain embodiments, the plurality of OCT images comprise optical coherence tomography angiography (OCTA) images. In certain embodiments, the system is configured to align the plurality of OCT images in a three-dimensional coordinate space. In certain embodiments, the system is configured to account for movement of the biological material during generation of the plurality of OCT images by the OCT scanner. In certain embodiments, the movement comprises at least one of translational movement and rotational movement. In certain embodiments, the one or more superficial layers comprise well-defined features or landmarks. In certain embodiments, the well-defined features or landmarks comprise blood vessels.

In some embodiments, a computer-implemented method for obtaining and processing images of a biological material as disclosed herein can comprise: generating, by an optical coherence tomography (OCT) scanner, a plurality of OCT images; accessing, by a computer system from the OCT scanner, the plurality of OCT images; generating, by the computer system, a plurality of enface images of one or more superficial layers of the biological material and a plurality of enface images of one or more deep layers from the plurality of OCT images; applying, by the computer system, one or more image registration techniques to the plurality of enface images of the one or more superficial layers to produce image alignment settings; storing, by the computer system, the image alignment settings; generating, by the computer system, an averaged enface image of each of the one or more deep layers by applying one or more image registration techniques, based at least in part on the stored image alignment settings, to the plurality of enface images of the one or more deep layers; and outputting, by the computer system, the one or more averaged enface images, wherein the computer system comprises a computer processor and an electronic storage medium.

In certain embodiments, the image registration techniques comprise at least one of linear registration, affine registration, and elastic registration. In certain embodiments, the method further comprises dividing each of the plurality of enface images of the one or more superficial layers and each of the plurality of enface images of the one or more deep layers into a plurality of sectors, and wherein the method further comprises applying registration to each of the plurality of sectors individually. In certain embodiments, the biological material comprises retinal, choroid, or another eye tissue. In certain embodiments, the one or more superficial layers comprise at least a superficial vascular plexus. In certain embodiments, the one or more deep layers comprise at least one of a choriocapillaris and deep capillary plexus. In certain embodiments, the plurality of OCT images comprise optical coherence tomography angiography (OCTA) images. In certain embodiments, the method further comprises aligning the plurality of OCT images in a three-dimensional coordinate space. In certain embodiments, the method further comprises accounting for movement of the biological material during generation of the plurality of OCT images by the OCT scanner. In certain embodiments, the movement comprises at least one of translational movement and rotational movement. In certain embodiments, the one or more superficial layers comprise well-defined features or landmarks. In certain embodiments, the well-defined features or landmarks comprise blood vessels.

In some embodiments, a computer-implemented method for obtaining and processing images of a biological material as disclosed herein can comprise: accessing or obtaining, by a computer system a plurality of OCT images generated by an OCT scanner; generating, by the computer system, a plurality of enface images of one or more superficial layers of the biological material and a plurality of enface images of one or more deep layers from the plurality of OCT images; applying, by the computer system, one or more image registration techniques to the plurality of enface images of the one or more superficial layers to produce image alignment settings; generating, by the computer system, an averaged enface image of each of the one or more deep layers by applying one or more image registration techniques, based at least in part on the stored image alignment settings, to the plurality of enface images of the one or more deep layers; and transmitting, by the computer system, the one or more averaged enface images for causing display of the one or more averaged enface images by an output device, wherein the computer system comprises a computer processor and an electronic storage medium.

In certain embodiments, the image registration techniques comprise at least one of linear registration, affine registration, and elastic registration. In certain embodiments, the method further comprises dividing each of the plurality of enface images of the one or more superficial layers and each of the plurality of enface images of the one or more deep layers into a plurality of sectors, and wherein the method further comprises applying registration to each of the plurality of sectors individually. In certain embodiments, the biological material comprises retinal, choroid, or another eye tissue. In certain embodiments, the one or more superficial layers comprise at least a superficial vascular plexus. In certain embodiments, the one or more deep layers comprise at least one of a choriocapillaris and deep capillary plexus. In certain embodiments, the plurality of OCT images comprise optical coherence tomography angiography (OCTA) images. In certain embodiments, the method further comprises aligning the plurality of OCT images in a three-dimensional coordinate space. In certain embodiments, the method further comprises accounting for movement of the biological material during generation of the plurality of OCT images by the OCT scanner. In certain embodiments, the movement comprises at least one of translational movement and rotational movement. In certain embodiments, the one or more superficial layers comprise well-defined features or landmarks. In certain embodiments, the well-defined features or landmarks comprise blood vessels.

In some embodiments, a system for obtaining and processing images of a biological material comprises: an imaging device configured to generate a plurality of three-dimensional images; one or more computer readable storage devices configured to store a plurality of computer executable instructions; and one or more hardware computer processors in communication with the one or more computer readable storage devices and configured to execute the plurality of computer executable instructions in order to cause the system to: access, from the imaging device, the plurality of three-dimensional images; generate, from the plurality of three-dimensional images, a plurality of enface images of one or more superficial layers of the biological material and a plurality of enface images of one or more deep layers of the biological material; apply one or more image registration techniques to the plurality of enface images of the one or more superficial layers to produce image alignment settings; store the image alignment settings; generate at least one averaged enface image of each of the one or more deep layers by applying one or more image registration techniques, based at least in part on the stored image alignment settings, to the plurality of enface images of the one or more deep layers; and output the one or more averaged enface images.

In some embodiments, a specialized optical coherence tomography imaging system for generating clearer medical images at deep tissue layers comprises: an imaging device configured to generate a plurality of three-dimensional images; a processor; an electronic storage device, the processor in electronic communication with electronic storage device configured to store the plurality of three-dimensional images; the processor configured to align a first tissue layer of each of the plurality of three-dimensional images to generate alignment data across the plurality of three-dimensional images; the processor configured to use the alignment data to align a second tissue layer of each of the plurality of three-dimensional images; the processor to perform image averaging to the aligned second tissue layers of each of the plurality of three-dimensional images to generate a clearer medical image of the second tissue layer; the processor configured to output the clearer medical image of the second tissue layer.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

The features, aspects and advantages of the embodiments of the inventions are described in detail below with reference to the drawings of various embodiments, which are intended to illustrate and not to limit the inventions. The drawings comprise the following figures in which:

FIG. 4 is a schematic diagram illustrating an example embodiment of OCT angiography image averaging;

FIG. 11 comprises a table illustrating experimental data presenting differences in the flow voids size and number between images with and without OCT imaging angiography image averaging;

DETAILED DESCRIPTION

Figure 1:
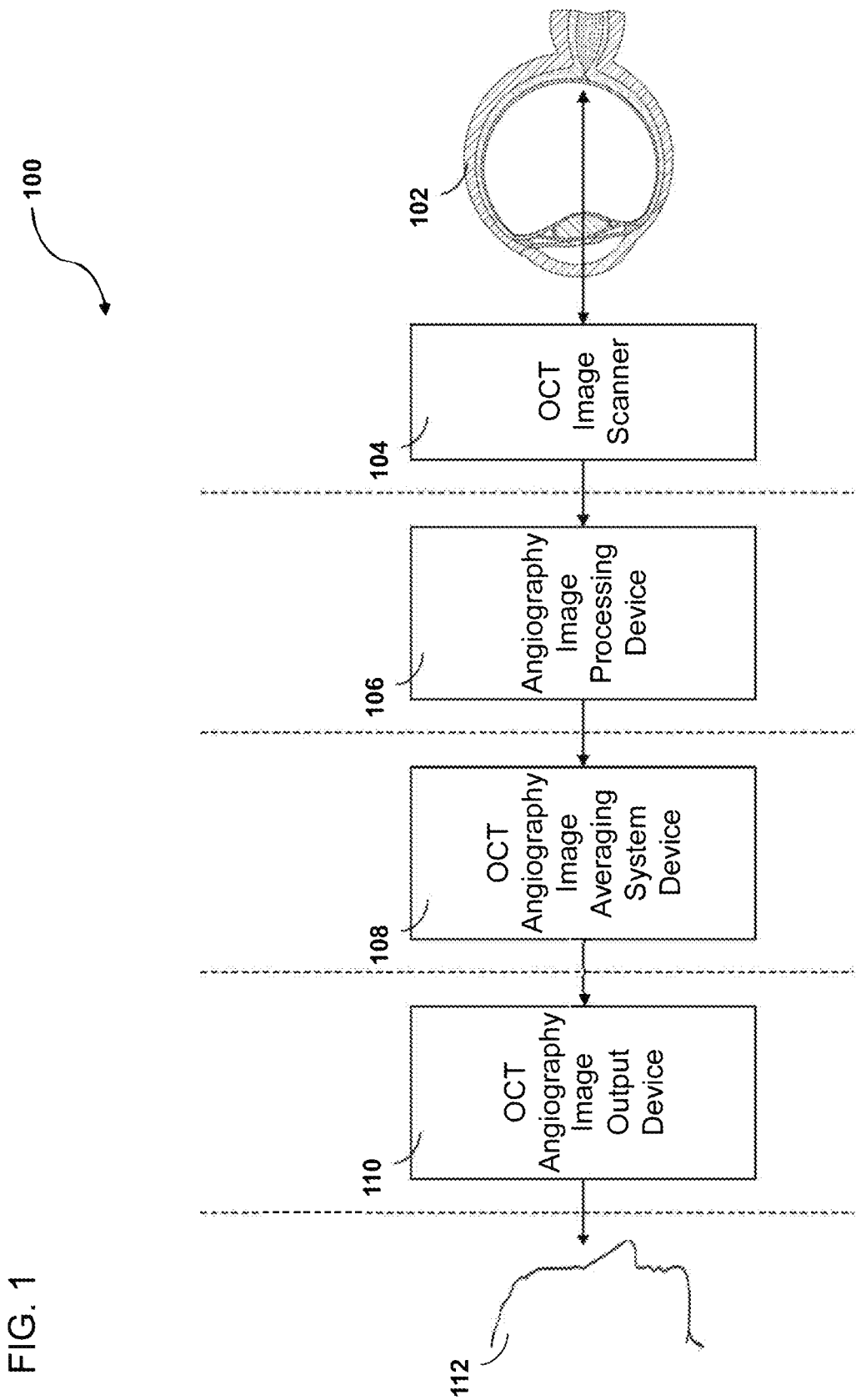
FIG. 1 is a block diagram depicting an example embodiment of an imaging system employing one or more of the OCT Angiography Image Averaging Processor systems, methods, and devices disclosed herein.

Optical coherence tomography angiography (OCTA) is an imaging technique that generates volumetric images of ocular tissue. These images can be useful for various purposes, including diagnosis, identification of ocular pathologies, surgical planning, and post-operative analysis, among other applications. However, in order for OCTA images to be useful for these purposes, they must have a high level of quality, precision, and/or clarity such that the detailed microvasculature of the ocular tissue can be perceived accurately. Thus, it can be critical that flaws such as image artifacts and/or motion noise and/or image misalignment and/or patient motion are minimized. Furthermore, since OCTA produces volumetric images, which can be segmented into enface images of individual ocular layers, it is desirable to minimize flaws and improve imaging quality of enface images of all layers. The disclosure herein provides systems, methods, and devices for improving the image quality and/or the enface image quality of OCT and/or OCTA or other three-dimensional imaging techniques.

Generally, a plurality of OCT and/or OCTA volumetric images of a patient's ocular tissue can generated by an OCT scanner. These volumetric images can then be converted into a plurality of image and/or enface images of individual layers. For example, the systems, methods, and devices disclosed herein could generate a plurality of images or enface of images of the superficial capillary plexus and a plurality of images or enface images of the choriocapillaris. At any point, these images or enface images can be processed, for example, by cropping, brightening, adding contrast, or any desired techniques. However, regardless of whether the images or enface images are processed because of motion of the patient during scanning, decorrelation signal loss, or otherwise, the plurality of images or enface images can have artifacts, inaccuracies, misalignment, blurriness, and other flaws.

In order to minimize these inaccuracies and/or flaws, the plurality of images or enface images of each individual layer can be aligned and averaged. The techniques utilized by the systems, methods, and devices disclosed herein for minimizing image flaws or the like can comprise sectoring, registration, and/or averaging. In some embodiments, sectoring refers to the process of segmenting each the plurality of images or enface images into a plurality of pieces or sections or quadrants or areas. Because, in some embodiments, the ocular structure or layer being imaged can require a very high level of precision in the accuracy of a registration or alignment, the sectoring process may be completed in order to provide greater exactness or preciseness in aligning images. Registration refers to the process of transforming each of the plurality of corresponding sectors of each of the plurality of images or enface images of a given layer into a single coordinate system. For example, each of the plurality of image or enface images of the superficial capillary plexus can be sectored into a plurality of pieces or sections, with each piece or section having a corresponding piece or section in each of the images or enface images that are sectored. Each piece or section can then undergo a registration process, including at least one of linear registration, affine registration, and/or elastic registration, which can utilize various features, for example, blood vessel size and/or y-branches and/or other characteristics, within the images to align the corresponding pieces into one coordinate system while accounting for the three-dimensionality of the imaged structure. In some embodiments, the generated coordinate system can be used to align image or enface images at different layers in the volumetric data set in order to align the images at the different layers. In some embodiments, after all the corresponding pieces are aligned pixel-to-pixel, they can undergo image averaging, in which the average intensities of the corresponding pixels can be plotted to produce a single, averaged, resultant image of the superficial capillary plexus once the pieces are recompiled. Alternatively, averaging can occur after recompilation of the pieces or sections.

In feature-rich layers such as the superficial capillary plexus, the registration can be completed accurately because the feature-based registration process can function by finding correspondence between image features such as points, lines, and contours. However, in some layers, for example the choriocapillaris, there can be an absence of a significant number of such features. As such, completing registration of feature-deficient layers like the choriocapillaris can be difficult. The systems, methods, and devices disclosed herein solve this problem by recognizing that because of the manner in which OCT volumetric images are acquired, that is linearly point-by-point from the surface to the subsurface, the registration data acquired during registration of the superficial capillary plexus layer (or other feature-rich layer) images can be identically or similarly applied to the images of the choriocapillaris (or other layers) to produce an accurate and clear image or enface image of that layer as well using imaging averaging and/or other techniques.

The disclosure herein provides systems, methods, and devices for improving optical coherence tomography machine outputs through multiple enface optical coherence tomography angiography averaging techniques. The embodiments disclosed herein can be utilized in ophthalmology for employing optical coherence tomography (OCT) for in vivo visualization of blood vessels and/or the flow of blood in an eye of a patient, which is also known generally as optical coherence tomography angiography (OCTA). The embodiments disclosed herein can be compatible with all types of three-dimensional image data. In some embodiments, the systems, methods, and devices disclosed herein are compatible with spectral domain OCT, swept source OCT, and any other type of three-dimensional imaging OCT. The embodiments disclosed herein can use linear registration, affine registration and/or elastic registration to align a plurality of optical coherence tomography angiography images or videos at corresponding superficial vascular layers having well-defined features or landmarks, and to apply the same linear registration, affine registration and/or elastic registration settings and/or data to corresponding deeper tissue layers, such as the choriocapillaris, which generally do not have well-defined features or landmarks, in order to align a plurality of corresponding deeper tissue layers for the purpose of averaging the images or video to produce a clearer and more accurate image or video of the tissue structure at deeper tissue layers.

The choriocapillaris is the capillary plexus of the choroid located between Sattler's layer and Bruch's membrane of an eye. It forms a dense freely anastomosing monolayer network of relatively large capillaries and serves as the major source of nutrition for the retinal pigment epithelium (RPE)

and outer retinal layers. Considering that a large number of studies, both clinical and histopathologic, has suggested a relationship between the choroidal circulation and retinal disorders including age-related macular degeneration and diabetic retinopathy, in vivo imaging of choriocapillaris is thought to be of value.

However, imaging of the choriocapillaris in vivo is challenging with existing technology. Although dye-based angiography, in particular indocyanine green angiography, has long been considered the gold standard for evaluation of the choroidal circulation, the limited depth resolution has made it difficult to resolve the choriocapillaris from the deeper vascular layers. In addition, the relatively low lateral resolution of conventional fundus imaging makes it difficult to resolve the inter-vascular spaces and visualize the choriocapillary network itself. Instead, with fluorescein angiography for example, early diffuse leakage through the fenestrated choriocapillaris only allows the choriocapillaris to be visualized as a diffuse grayish haze, the so-called "choroidal blush."

Optical coherence tomography angiography (OCTA) offers a visualization of the retinal microvasculature of the fundus through motion contrast derived by detecting the reflectivity changes between multiple OCT B-scans. Unlike dye-based angiography, OCTA is free from limitations due to dye leakage, and has a sufficiently high axial resolution such that enface images from the choriocapillaris layer can be selectively extracted. On the other hand, current OCTA technology still suffers from relatively low lateral resolution. The effect of enface image averaging on the choriocapillaris layer as disclosed in the systems, methods, and devices disclosed herein increases this resolution.

The unique granular appearance of the choriocapillaris layer can be useful in distinguishing it from other layers, such as the larger choroidal vessel layers, or the projection artifacts of the retinal vessels on the RPE layer, as well as for qualitative assessment of choriocapillaris alterations. However, a granular appearance without resolution of the capillaries themselves may not allow for more detailed morphologic evaluations of this circulation. In some embodiments, the registration and alignment process as disclosed herein can enhance image quality. In some embodiments, a poorly-defined granular image appearance as observed in single unaligned images can be transformed to a meshwork pattern which more closely resembles a histological image of human choriocapillaris through the systems, methods, and devices disclosed herein. Similarly, in some embodiments, the resultant images of the registration and alignment processes disclosed herein show a morphologic pattern which more closely mimics the meshwork pattern observed on histology and potentially allows more precise quantitative metrics to be generated. For example, the resultant images generated by the systems, methods, and devices disclosed herein may share similarities to histologic morphometric assays in characteristics such as the mean vessel caliber, the lobular pattern arrangement, vessel diameter, vessel density, and angioarchitecture pattern, among others. In some embodiments, given that the caliber of the choriocapillaris may be affected by diseases such as AMD, OCTA image averaging as disclosed herein may allow such alterations to be studied more precisely.

In some embodiments, the registration and alignment process as disclosed herein may remove noise caused at least in part by decorrelation signal loss, allowing more accurate imaging of the granular pattern and flow voids in the choriocapillaris.

The disclosure herein also provides methods, systems, and devices for improving cross-sectional and three-dimensional visualization of ocular tissues using OCT imaging. The embodiments disclosed herein can be utilized in the identification and assessment of retinal abnormalities, in the performance of volumetric and retinal thickness analysis, and/or the evaluation of surgical and/or pharmacological interventions.

It should be noted that while the disclosure herein illustrates applying the systems, methods, and devices herein to retinal tissue and/or choroid tissue, by way of example only, one of ordinary skill in the art would appreciate that the systems, methods, and devices disclosed herein can be applied to other tissues in the eye, whether posterior or anterior eye wall tissue (for example, the sclera), or tissues outside the eye, or to non-tissue materials.

Optical coherence tomography is a technique that generally uses light directed at translucent or opaque or partially-opaque materials, such as tissue, and a portion of the light is reflected from or scattered off the sub-surfaces of the material. The reflected or scattered light is analyzed using low-coherence interferometry to generate in vivo cross sectional and three-dimensional images of the material. In generating such images, optical coherence tomography data is acquired linearly point-by-point. Each point comprises data describing the material starting from the surface of the material to the subsurface of the material, and in other words, each point is an axial depth scan of the material, which is generally known as an A-scan. By combining a linear series of adjacent or nearby A-scans, a cross-sectional OCT image, known generally as a B-scan, can be generated. The combination of B-scans can be used to construct a three-dimensional image (C-scan) of the material.

Accordingly, optical coherence tomography generates reconstructive images of an analyzed material. In other words, OCT data is acquired linearly through an analyzed material, such as retinal tissue, from the superficial to the deep in single lines, termed A-scans. Each pixel in an image is obtained from each line of OCT data, and depending on the desired depth of view, different data points along each line of OCT data, from the superficial to the deep, is used to construct an image.

Due to the way OCT data is collected, the OCT data at and between the superficial surface layer and the deep surface layer are aligned. The alignment of such OCT data can allow one set of OCT data of a material to be aligned with another set of OCT data of the same material. The alignment of different sets of OCT data of the same material can enable data averaging at all layers of depth, which can help generate clearer images with greater definition, especially at deeper depth layers where the raw OCT data can be of lower quality and/or of lower resolution.

The challenge of improving the image quality at deeper depth layers of the OCT data is aligning images at the deeper depth levels because, in general there are no or few landmarks or features or characteristics that can be used to align the OCT data sets. To overcome this challenge, the systems disclosed herein can be configured to align different OCT data sets by utilizing superficial layers where there are significant landmarks, features, and/or characteristics that can be used to align different OCT data sets. In some embodiments, features such as vessel characteristics, including for example, vessel branching, y-features (points at which a vessel splits), terminal vessels, vessel patterns, vessel terminations, vessel sizes, vessel width, vessel tips, vessel location, and any other features can be utilized in the registration of the superficial layer. By aligning different OCT data sets at corresponding superficial layers for each data set, the systems disclosed herein can be configured to utilize the alignment data settings at the superficial layers and apply such alignment data settings to different depth layers, such as deeper depth levels, of the OCT data sets. Alternatively, the system can be used to align the entire three-dimensional data set, wherein the system can access the different depth layers desired for averaging and viewing.

In some embodiments, the systems disclosed herein can be used in ophthalmology. In some embodiments, the systems can be configured to analyze ophthalmic OCTA images and video, which generally relates to using OCT to better visualize the blood vessels and the flow of blood in the eye. In general, OCTA images show clear and accurate retinal vasculature; however, certain systems, methods, and devices disclosed herein are configured for further improving the quality of OCTA images and videos. In some embodiments, the system is configured to access multiple images and/or videos and average the images and/or videos. In some embodiments, the averaging of the multiple images and/or videos involves superimposing images and/or videos such that they lay on top of one another in order to remove noise and/or improve signal and/or improve the overall quality of the images and/or videos. In some embodiments, the system is configured to average cross-sectional images and/or videos, and/or three-dimensional images and/or videos, generated from OCT machines.

In general, OCT images can be viewed as cross-sectional images, meaning that the images are being viewed through the layers of the retina on edge, which is how OCT data is frequently viewed. Generally, OCT data can also be viewed and analyzed by looking at the OCT image in an enface manner, in other words, looking at the surface of the material being described by the OCT data. In some embodiments, the systems disclosed herein are configured to analyze enface images/videos of the OCT data in order to better examine blood vessels of retinal tissue. In some embodiments, the systems disclosed herein are configured to average a plurality of enface OCTA images and/or videos.

In some embodiments, the systems herein pre-process the enface images before performing a registration or alignment. This pre-processing may involves removing features below a certain level of brightness or clipping off portion of the image, among other functions. In some embodiments, the system is configured to average the OCTA images and/or video to produce a better visualization of one of the deepest layers of retina, which generally is the choriocapillaris. Generally, the choriocapillaris is thought to be a very important structure of the eye relevant to many retinal diseases and abnormalities. In general, the choriocapillaris is part of the choroid and is one of the inner most layers of the choroid, which is situated adjacently and externally to the retina, and internally to the sclera. In general, the choroid is a relatively thin, highly pigmented, vascular loose connective tissue layer. Generally, the choroid can comprise melanocytes and extend from the optic nerve to the ciliary body and can range in thickness from ~0.3 millimeters to about ~0.1 millimeters.

In order to improve visualization of the choriocapillaris, or any other layer of the retina or the choroid or other posterior eye wall tissue or any other eye tissue layer, the system in some embodiments is configured to align images of the superficial retinal vasculature, which is the portion of the retinal vasculature visible within the superficial layers of the retina visible on OCT images. It can be important to use the superficial alignment because if disparate OCT data sets that are not aligned are averaged, the image produced from such a process would generally yield inaccurate, blurry, unusable images. In some embodiments, the system is configured to align images and/or video by using the superficial retinal vasculature, where the vessels are visible, and the retina to align the images and/or videos. In some embodiments, the system is configured to use the same alignment information from the superficial retinal vasculature and apply the alignment information to images from deeper tissue layers, such as the choriocapillaris, which generally do not have many vessel features. In general, the choriocapillaris on unaveraged OCTA images is relatively featureless and has vessels that are very small and difficult to distinguish. Accordingly, an alignment based on relatively small features of the choriocapillaris would generally be challenging because it would be akin to using an image comprising thousands of small dots and trying to determine how match and superimpose such dots from one OCT data set onto corresponding dots from a different OCT data set.

In some embodiments, the system is configured to use the alignment information for the superficial retina layer of the OCT data sets being examined and apply the same alignment information to the deeper retinal and/or choroidal layers, such as the choriocapillaris layer, of the same OCT data sets in order to optimize signal to noise of the deeper retina layer. In other words, the system can be configured to access a line of information from one layer and use that information to improve the quality of another deeper layer.

In some embodiments, the system is configured to align a plurality of OCT data sets in the X, Y, and Z coordinate space. In other words, the system can be configured to align images and/or videos by accounting for the 3-dimensional nature of the material being analyzed. In some embodiments, the system is configured to align different sets of images and/or videos while accounting for patient movement due to translation. For example, translation meaning movement in the X and Y directions, which could include up and down, side to side displacement that the system can be configured to account for during realignment of the images and/or video. In some embodiments, the system is configured to account for patient head tilt movement or any other patient movement in the Z direction or axis. For example, during imaging of a patient there could be rotation of the patient along the Z axis and in some embodiments, the system is configured to compensate for rotation as well as for translation. In general, the accounting for this combination of translation and rotation can be called linear registration, which can include affine registration. Based on conducted experiments and research, a system that just performs a linear registration or an affine registration to align the images and/or video of the superficial retina generates images and/or video with mismatches and misalignment. In general, linear registration or linear transformation refers to transformations that include rotation, scaling, translation, and affine transforms.

Such mismatches and misalignments can result from not accounting for and compensating for the fact that the retina (and other materials) is not a flat structure, but rather the retina is a three-dimensional structure. When there are slight differences in the angle which the light from an OCT imaging system intersects with the retina, the three-dimensionality of the retina causes another type of displacement or retraction or scattering of the light which has to be compensated. In some embodiments, the system is configured to account for such light scattering due to the three-dimensional nature of a material being examined by performing elastic registration. In some embodiments, the system is configured to perform a combination of linear and/or affine registration and elastic registration. In some embodiments, the system is configured to perform linear and/or affine registration and elastic registration on a plurality of OCTA images and/or video in order to obtain alignment of the superficial retina layer in the plurality of the OCTA images and/or videos for the purpose of applying the same transformation to a deeper retina layer.

In some embodiments, the elastic registration involves making an estimation of the geometry and curvature of the ocular tissue or other biological material being imaged to predict the position of certain pixels or features within related images. In some embodiments, the elastic registration involves making assumptions regarding the curvature and the topography of a retinal surface. In some embodiments, raw and/or processed OCT image data can be used in the alternative or in addition to estimations and assumptions in order to improve the elastic registration. In some embodiments, elastic registration can be critical in obtaining an accurate and clear resultant image.

In some embodiments, in non-linear (elastic) registration, dissimilarity of image gray values between a reference image and a target image is calculated (using a mathematical operation such as subtraction or division) and then the target image is deformed to minimize this difference. Because the similarity (or dissimilarity) is defined by this image difference, there are potentially infinite specific image features. In some embodiments, y-features or the vessel branches are more useful for accurate image registration than a granular pattern as found in images of the choriocapillaris or homogeneous flat intensity region like the foveal avascular zone. In some embodiments, the elastic registration may involve epipolar geometry, known image acquisition positions, and/or positional data, to reconstruct surface topography of ocular tissue based on the differences between two or more images.

In some embodiments, the system is configured to use linear and/or affine registration and elastic registration to align OCTA images in the superficial vasculature layer having well defined features or landmarks and to apply the same linear and/or affine registration and elastic registration settings and/or data to a deeper tissue layer, such as the choriocapillaris, that does not have well defined features or landmarks. In some embodiments, completing registration and alignment at a superficial layer can facilitate registration at a lower layer by using the registration data obtained from the registration of the superficial layer. In some embodiments, this process can be completed using for example, a transformation matrix. In some embodiments, there is an assumption that the lower layers move in the same manner as the upper layers, and thus the registration of the superficial layers can be applicable to aligning the lower layers. In some embodiments, this alignment process can match corresponding pixels in various images of different layers of the same ocular tissue to make an accurate alignment of the images. In some embodiments, once the corresponding pixels are matched, the average intensities of the corresponding pixels can be plotted in a single image to produce a single, averaged, resultant image.

In some embodiments, the system is configured to take registration information at one layer, for example, the superficial retina layer having nice large identifiable blood vessels that can be used as landmarks or features to align OCTA images and/or video. In general, deeper layers, for example, the choriocapillaris, generally lacks significant landmarks or features that can be used for alignment purposes because such deeper layers often look like ground glass or a plurality of little tiny little dots where it is difficult to discern one dot from another. Because the way the OCT data is acquired, registration alignment settings used for one layer can be applied at a different layer of the OCT data sets. In general, OCT images are reconstructive images because OCT images are generated by acquiring OCT data linearly or vertically through the material, such as the retina, from the superficial to the deep in single lines. Each pixel is counted by going line by line, wherein each line goes from the superficial to the deep. Accordingly, the data at the superficial layer can be automatically aligned with the data at the deeper layers by virtue of the data acquisition process.

In some embodiments, the system is configured to take the alignment of the superficial layer of the OCT data set and apply the alignment to a deeper layer of the OCT data set in order to perform image and/or video averaging. In some embodiments, the system is configured to perform additional image processing, such as contrast enhancement, contrast limited adaptive histogram equalization, and/or minimum intensity operations.

In some embodiments, the system can be implemented in specialized software code or machine code configured to perform one or more or all of the processing blocks disclosed herein in order to generate improved OCTA images of various retinal and/or choroidal layers including the choriocapillaris.

In some embodiments, the system employs one or more macro program blocks. In some embodiments, the system can be implemented with a macro written for the imaging viewing system application Image J. In some embodiments, the one or more macro program blocks comprises cropping a plurality of images to generate a plurality central rectangular specified area of pixels, for example 950 by 900 pixels or of any other size, performing linear or affine image registration on images of the superficial layer or layers to align position gaps, for example, by using plug-in, Stackreg (http://bigwww.epfl.ch/thevenaz/stackreg/), storing the affine or linear registration information into a database, and accessing in the database, the saved registration information for applying to deeper tissue layer images (deep capillary plexus and choriocapillaris). In some embodiments, the registration can be computed on the superficial capillary plexus video. In some embodiments, the one or more macro program blocks further comprises accessing, in the database, the saved registration information for applying to the other tissue image layers. In some embodiments, to further increase the accuracy of the registration, the images/videos can be divided into 9 sectors; in other embodiments, more or less sectors can be used. In some embodiments, elastic image registration can be performed to correct for distortions by using the combination of two ImageJ plug-ins, bUnwarpJ and Feature Extraction. In some embodiments, the elastic registration can be performed on every sector individually. In some embodiments, the registration is computed on the superficial capillary plexus video. In some embodiments, the one or more macro programming blocks further comprises storing the elastic registration information into a database, accessing, in the database, the saved elastic registration information for applying to the other layers, and stitching together the 9 registered videos to reconstruct the original size registered video; in some embodiments, the 9 sectors have some overlaps and can require that the overlapped margins be cut before stitching the 9 vectors together In some embodiments, the system can use information obtained from a registration of a superficial layer of a tissue to better align images of a deeper layer of the ocular tissue. In some embodiments, the system can use alignment data obtained from a superficial layer of an ocular tissue to align images of a choriocapillaris. In some embodiments, the registration techniques can comprise elastic registration to account for the three-dimensionality of the imaged structure. In some embodiments, the registration techniques must involve elastic registration to account for the three-dimensionality of the ocular tissue being imaged.

In some embodiments, the system can consider the vessel density of a resultant image to determine the accuracy of an alignment. In some embodiments, a higher vessel density can indicate misalignment of the enface images and poor resultant image quality. In some embodiments, the vessel density can be computed as the area occupied by vessels divided by the overall image area. In some embodiments, a lower vessel density in the resultant image is preferred and indicates a more accurate alignment.

FIG. 1 illustrates a block diagram depicting an example embodiment of an imaging system employing certain OCT angiography image averaging processor systems disclosed herein. In some embodiments, the example OCT angiography image averaging processor system 100 comprises an OCT image scanner 104 for acquiring or generating image data of ocular tissue of a patent 102.

In some embodiments, the system can generate or obtain a plurality of images of ocular tissue of a patient. In some embodiments, the number of the plurality of images of ocular tissue can be about 3. In some embodiments, the number of the plurality of images of ocular tissue can between about 1 and 100. In some embodiments, the number of the plurality of images of ocular tissue can be about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100, or any value between any of the aforementioned values, and/or within a range defined by any of the aforementioned values.

In some embodiments, the system 100 further comprises an OCT angiography image processing device 106 for conducting pre-image processing on the generated or acquired image data. This pre-image processing may comprise alignment or registration of one or more superficial layers and/or one or more deeper layers. The alignment or registration may comprise one or more of linear registration, affine, registration, and/or elastic registration. In some embodiments, the system 100 further comprises an OCT angiography image averaging system device 108 which may also conduct registration, averaging, post-processing, and/or other functions on the pre-processed images. In some embodiments, the system 100 further comprises an OCT angiography image output device 110 for outputting or transmitting resultant images to a user 112. In some embodiments, the resultant images will be averaged composite images. In some embodiments, the user 112 can review the resultant images for various purposes, including diagnosis or identification of ocular pathologies or post-surgery assessment, among others.

Figure 2:
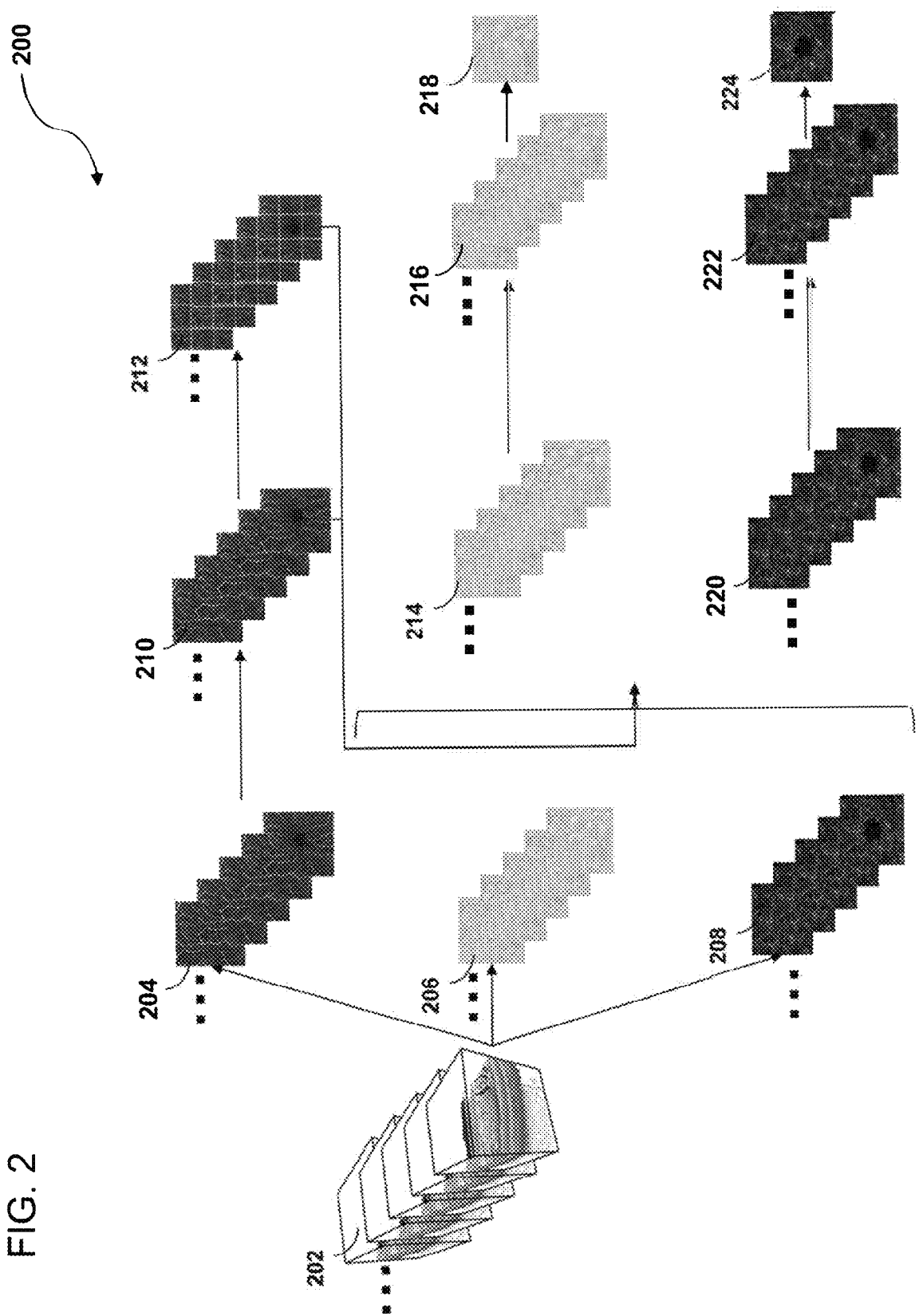
FIG. 2 is a schematic diagram illustrating an example embodiment of the OCT Angiography Image Averaging Processor systems disclosed herein.

FIG. 2 is schematic diagram illustrating another example embodiment of the OCT angiography image averaging processor systems disclosed herein. In some embodiments, the example OCT angiography image averaging processor system 200 can obtain a plurality of raw OCTA cube image data sets 202 of ocular tissue. In some embodiments, the system 200 can extract or obtain a plurality of enface or "slab" images of a superficial capillary plexus 204 from the plurality of raw OCTA cube image data sets 202. In some embodiments, the system 200 can further extract or obtain a plurality of enface or "slab" images of a choriocapillaris 206 from the plurality of raw OCTA cube image data sets 202. In some embodiments, the system 200 can further extract or obtain a plurality of enface or "slab" images of a deep capillary plexus 208 from the plurality of raw OCTA cube image data sets 202. In some embodiments, these enface images or "slabs" are 2-dimensional representations of a 3-dimensional data set.

In some embodiments, the system 200 can further apply linear image registration to the plurality of enface images of superficial capillary plexus 204 to align images and generate linear registration information 210. In some embodiments, the system 200 can further divide the plurality of enface images of superficial capillary plexus 204 into sectors and apply elastic image registration to the plurality of enface images of superficial capillary plexus to align images and generate elastic registration information 212.

In some embodiments, the system 200 can further apply the linear registration information 210 and elastic registration data 212 to the plurality of enface images of choriocapillaris 206 to obtain a plurality of sectored images of choriocapillaris 214. In some embodiments, the system 200 can further reconstruct the plurality of sectored images of choriocapillaris 214 into a plurality of complete aligned images of choriocapillaris 216. In some embodiments, the system 200 can generate an averaged image of choriocapillaris 218 based on the plurality of complete aligned images of choriocapillaris 216.

In some embodiments, the system 200 can further apply the linear registration information 210 and elastic registration data 212 to the plurality of enface images of deep capillary plexus 208 to obtain a plurality of sectored images of deep capillary plexus 220. In some embodiments, the system 200 can further reconstruct the plurality of sectored images of deep capillary plexus 220 into a plurality of complete aligned images of deep capillary plexus 222. In some embodiments, the system 200 can generate an averaged image of deep capillary plexus 224 based on the plurality of complete aligned images of deep capillary plexus 222.

In some embodiments, the system 200 can further generated averaged images of any number of layers of ocular tissue using the same steps disclosed herein with reference to FIG. 2.

Figure 3:
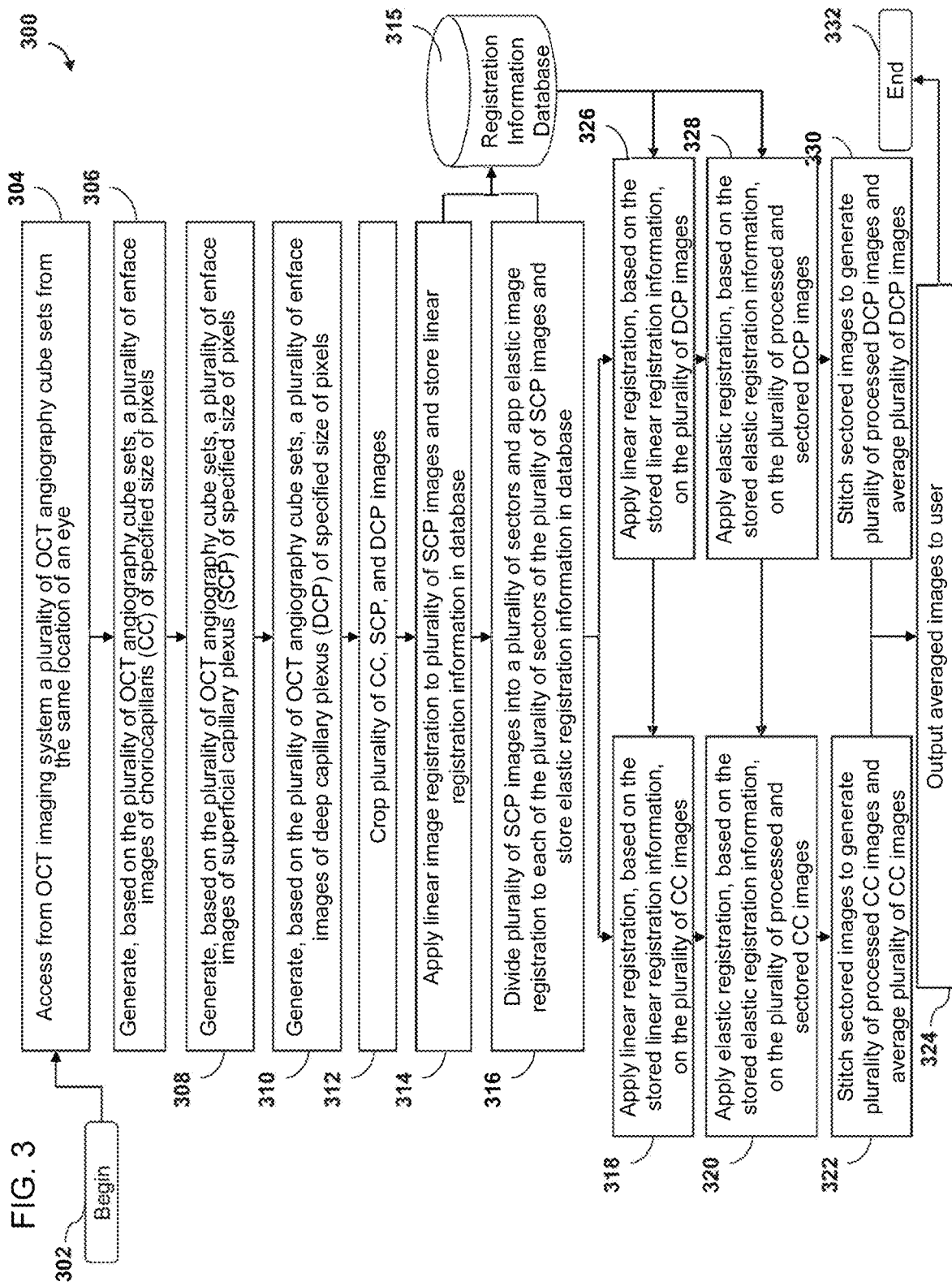
FIG. 3 is a flow chart depicting an example embodiment of a process for performing OCT angiography image averaging.

FIG. 3 is a flow chart depicting an example embodiment of a process 300 for performing OCT angiography image averaging. In some embodiments, the process 300 can begin by accessing, obtaining, or generating from an OCT imaging system a plurality of OCT angiography cube sets from the same location of an eye at 304. In some embodiments, at 306, based on the plurality of OCT angiography cube sets, a plurality of enface images of choriocapillaris (CC) of a specified size of pixels can be generated. In some embodiments, at 308, based on the plurality of OCT angiography cube sets, a plurality of enface images of superficial capillary plexus (SCP) of a specified size of pixels can be generated. In some embodiments, at 310, based on the plurality of OCT angiography cube sets, a plurality of enface images of superficial capillary plexus (SCP) of a specified size of pixels can be generated. In some embodiments, based on the plurality of OCT angiography cube sets, a plurality of enface images of other layers of ocular tissue can be generated.

In some embodiments, at 312, the plurality of CC, SCP, and DCP images can be cropped to obtain an image with a desired size, dimensions, and/or shape. In some embodiments, the plurality of images can be obtained from the same location or biological tissue of a patient. However, in some embodiments, movement of the patient causes the images to not be perfectly overlapped or aligned. In some embodiments, because of patient movement or otherwise, the plurality of images will not be perfectly aligned. In some embodiments, because of patient movement or otherwise, the features present in the plurality of images will not be perfectly aligned upon generating the images.

In some embodiments, to account for the initial misalignment of the images obtained by a scanner, the plurality of images are cropped. In some embodiments, this cropping process ensures that all of the same blood vessels are present and visible in each of the plurality of images. In some embodiments, the cropping process can be completed manually. In other embodiments, the cropping process can be automated by a computer or otherwise. In some embodiments, a crop size is specified, such that all images are cropped in the same manner and the cropped images are the same size.

In some embodiments, the cropped image dimensions can be about 3 mm by 3 mm. In some embodiments, each of the cropped images can comprise dimensions between about 0.3 mm by 0.3 mm to about 12.0 mm by 12.0 mm. For example, each cropped image can have dimensions of about 0.3 mm by 0.3 mm, 0.4 mm by 0.4 mm, 0.5 mm by 0.5 mm, 0.6 mm by 0.6 mm, 0.7 mm by 0.7 mm, 0.8 mm by 0.8 mm, 0.9 mm by 0.9 mm, 1.0 mm by 1.0 mm, 1.5 mm by 1.5 mm, 2.0 mm by 2.0 mm, 2.5 mm by 2.5 mm, 2.7 mm by 2.7 mm, 3.0 mm by 3.0 mm, 3.5 mm by 3.5 mm, 4.0 mm by 4.0 mm, 4.5 mm by 4.5 mm, 5.0 mm by 5.0 mm, 5.5 mm by 5.5 mm, 6.0 mm by 6.0 mm, 6.5 mm by 6.5 mm, 7.0 mm by 7.0 mm, 7.5 mm by 7.5 mm, 8.0 mm by 8.0 mm, 8.5 mm by 8.5 mm, 9.0 mm by 9.0 mm, 9.5 mm by 9.5 mm, 10.0 mm by 10.0 mm, 10.5 mm by 10.5 mm, 11.0 mm by 11.0 mm, 11.5 mm by 11.5 mm, 12.0 mm by 12.00, and/or within any range between the aforementioned values.

In some embodiments, the cropping process can be completed before alignment or registration. In other embodiments, the cropping process can be completed after alignment or registration. In some embodiments, cropping can be completed on each of a plurality of image sectors instead of or in addition to the overall composite images.

Referring again to FIG. 3, in some embodiments, at 314, a linear image registration can be applied to the plurality of SCP images and a linear registration information can be stored in one or more databases, including, for example, a registration information database 315. In some embodiments, at 316, the plurality of SCP images can be divided into a plurality of sectors and elastic image registration can be applied to each of the plurality of sectors of the plurality of SCP images and elastic registration information can be stored in one or more databases, including, for example, a registration information database 315. In some embodiments, linear registration can also be applied to each of the plurality of sectors of the plurality of SCP images.

In some embodiments, at 318, linear registration can be applied to the plurality of CC images based on the stored linear registration information. In some embodiments, at 320, elastic registration can be applied to the plurality of processed and sectored CC images, based on the stored elastic registration information. In some embodiments, linear registration can also be applied to each of the plurality of sectors of the plurality of processed and sectored CC images. In some embodiments, at 322, the plurality of aligned and sectored CC images can be recompiled or "stitched" back together to generate a plurality of whole processed CC images. In some embodiments, also at 322, the plurality of whole processed CC images can be averaged. In some embodiments, at 324, the averaged CC images can be outputted or transmitted to a user.

In some embodiments, at 318, linear registration can be applied to the plurality of DCP images based on the stored linear registration information. In some embodiments, at 320, elastic registration can be applied to the plurality of processed and sectored DCP images, based on the stored elastic registration information. In some embodiments, linear registration can also be applied to each of the plurality of sectors of the plurality of processed and sectored DCP images. In some embodiments, at 322, the plurality of aligned and sectored DCP images can be recompiled or "stitched" back together to generate a plurality of whole processed DCP images. In some embodiments, also at 322, the plurality of whole processed DCP images can be averaged. In some embodiments, at 324, the averaged DCP images can be outputted or transmitted to a user.

FIG. 4 is a schematic diagram illustrating an example embodiment of OCT angiography image averaging results 400. Unaveraged image 402 illustrates an optical coherence tomography angiography image before multiple enface image averaging. In unaveraged image 402, the vessels are discontinuous due to the decorrelation signal loss. Non-registered image 404 illustrates an example averaged OCT angiography image without registration. In some embodiments, averaging multiple unregistered frames can result in a blurred image due to misalignments between frames. Resultant image 406 illustrates an example OCT angiography image that has been registered and averaged. In some embodiments, an averaged image after registration shows more continuous vessels and less background noise compared to the single unaveraged image 402.

Figure 5B:
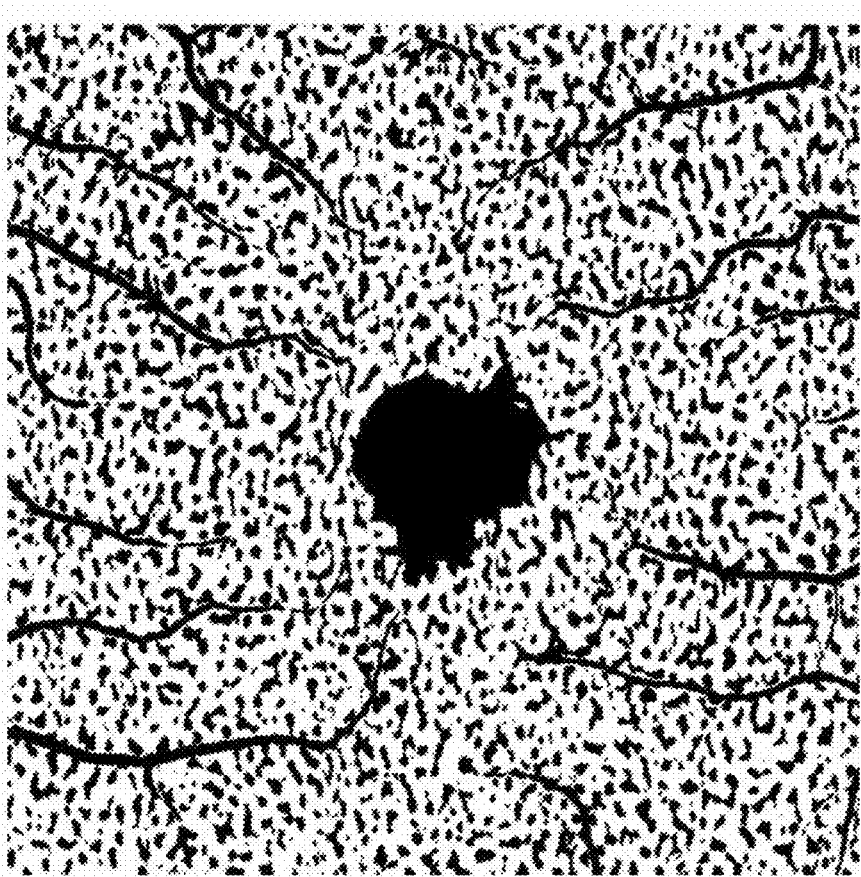
FIGS. 5A and 5B are example images illustrating binarized images generated from some embodiments of OCT angiography image averaging.
Figure 5A:
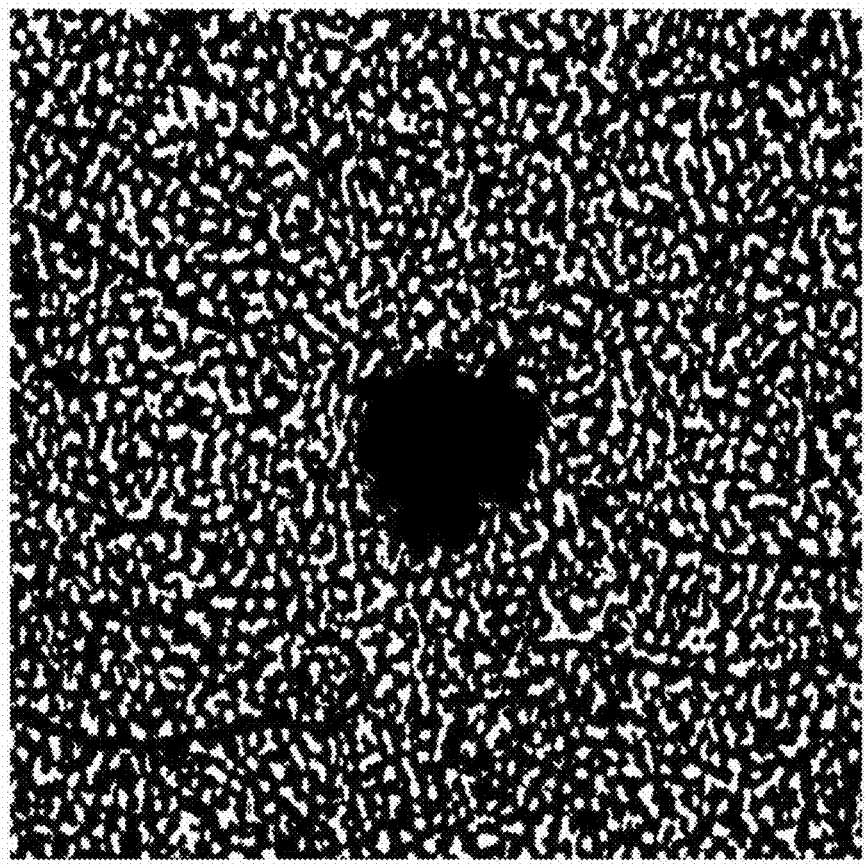

FIGS. 5A and 5B are example images illustrating binarized images generated from an embodiment of OCT angiography image averaging. In some embodiments, choriocapillaris OCTA images can be binarized for quantitative image analysis of the flow voids and the capillary vessel (vessel density, vessel length density vessel diameter index). FIG. 5A illustrates a choriocapillaris OCTA image binarized to analyze flow voids. FIG. 5B illustrates a choriocapillaris OCTA image binarized to analyze the capillary vessel.

Figure 6:
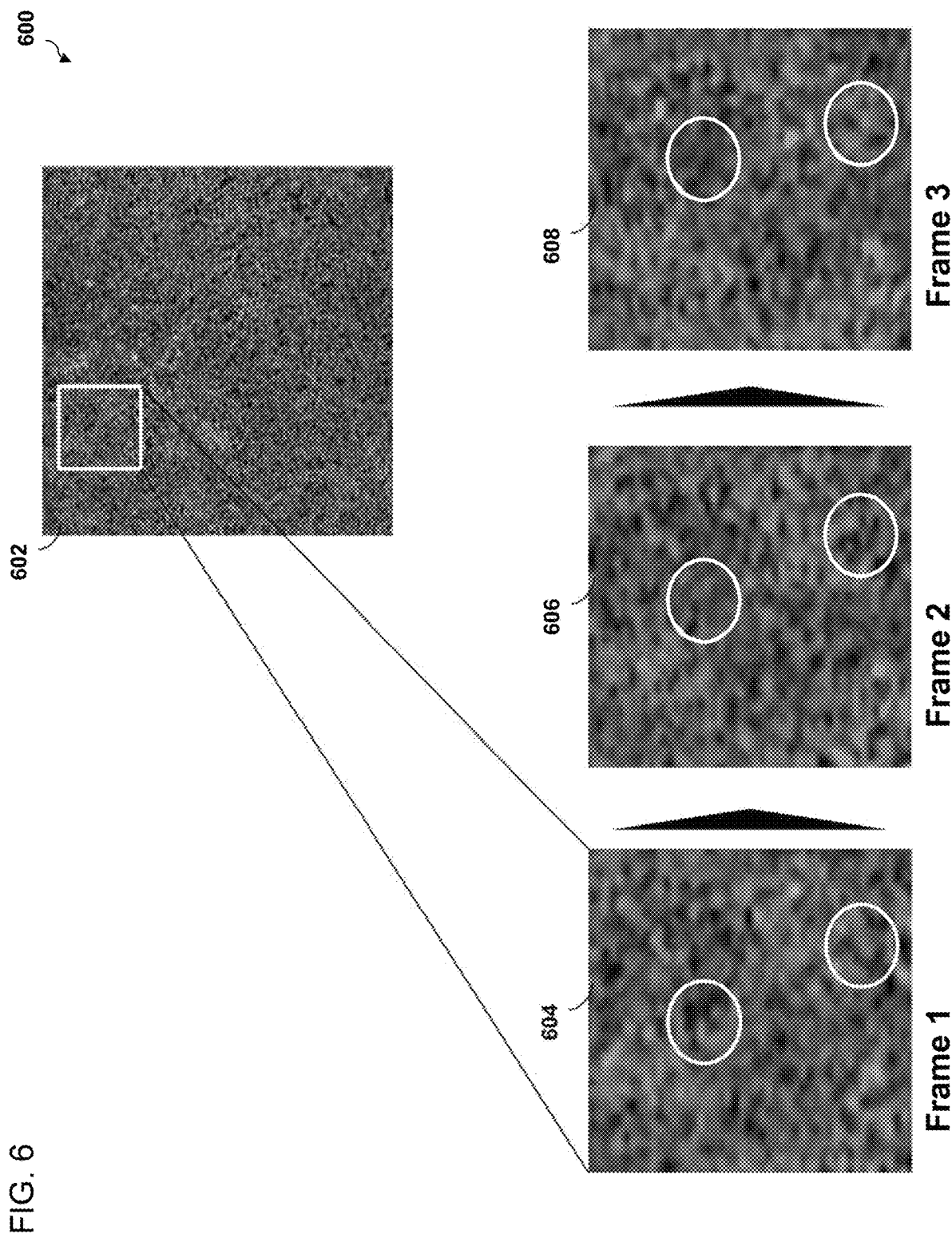
FIG. 6 comprises example images of multiple image frames illustrating the differences in flow void patterns between frames.

FIG. 6 comprises example images of multiple image frames illustrating the differences in flow void patterns between frames of OCTA images of a retinal tissue. Composite image 602 is an amalgamation of 9 images of a of retinal tissue created without utilizing the systems and processes disclosed herein. Frames 604, 606, and 608 are portions of individual images of retinal tissue that make up the composite image 602. The pattern (location, intensity and shape) of the small flow voids changes from frame 604 to frame 606 to frame 608. The pattern of flow voids may be influenced by the noise and the decorrelation signal loss (even in SRL, capillaries are discontinuous). The accuracy of the registration in composite image 602 can be poor because the layer does not contain any landmarks. The systems, methods, and devices disclosed herein solve this issue by utilizing registration information created by registration of a superficial layer having significant landmarks to increase the accuracy of registration of deeper layers.

Figure 7:
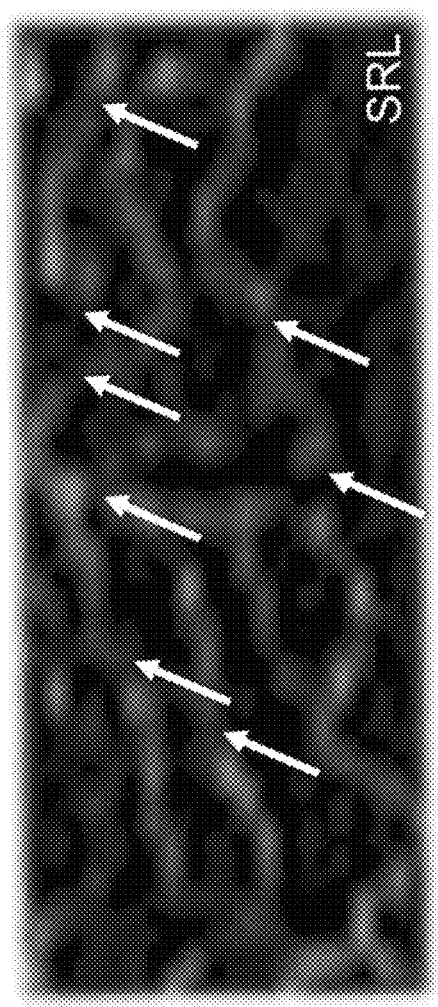
FIG. 7 is an example image illustrating how the pattern of the small flow voids can change from image frame to image frame, which can show the discontinuity (or the lack of decorrelation signals) of the vessels even in the superficial layers, and such discontinuity should appear in the other layers, for example, the choriocapillaris layer.

FIG. 7 is an example image 700 illustrating how the pattern of the small flow voids can change from image frame to image frame, which can show the discontinuity (or the lack of decorrelation signals) of the vessels even in the superficial layers, and such discontinuity should appear in the other layers, for example, the choriocapillaris layer.

Figure 8:
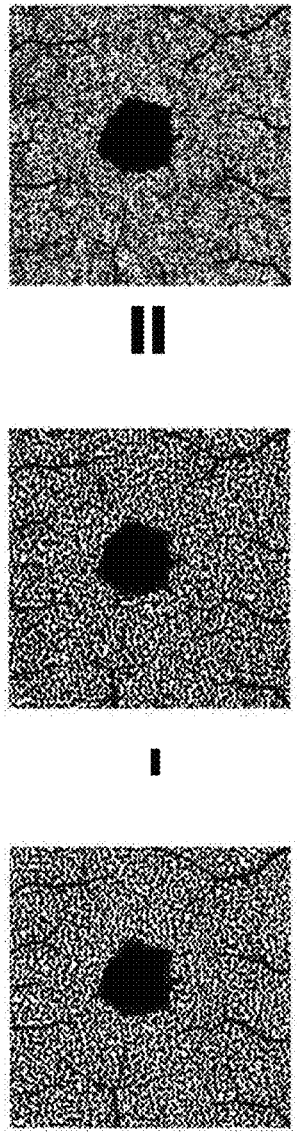
FIG. 8 comprises a table illustrating experimental data presenting differences in morphological parameters of the choriocapillaris among nine different OCT scans of an eye of a patient.

FIG. 8 comprises table 800 illustrating experimental data presenting differences in morphological parameters of the choriocapillaris among nine different OCT scans of an eye of a patient. The differences in the pattern of flow voids may be because of the noise and the decorrelation signal loss which differ from scan to scan.

Figure 9:
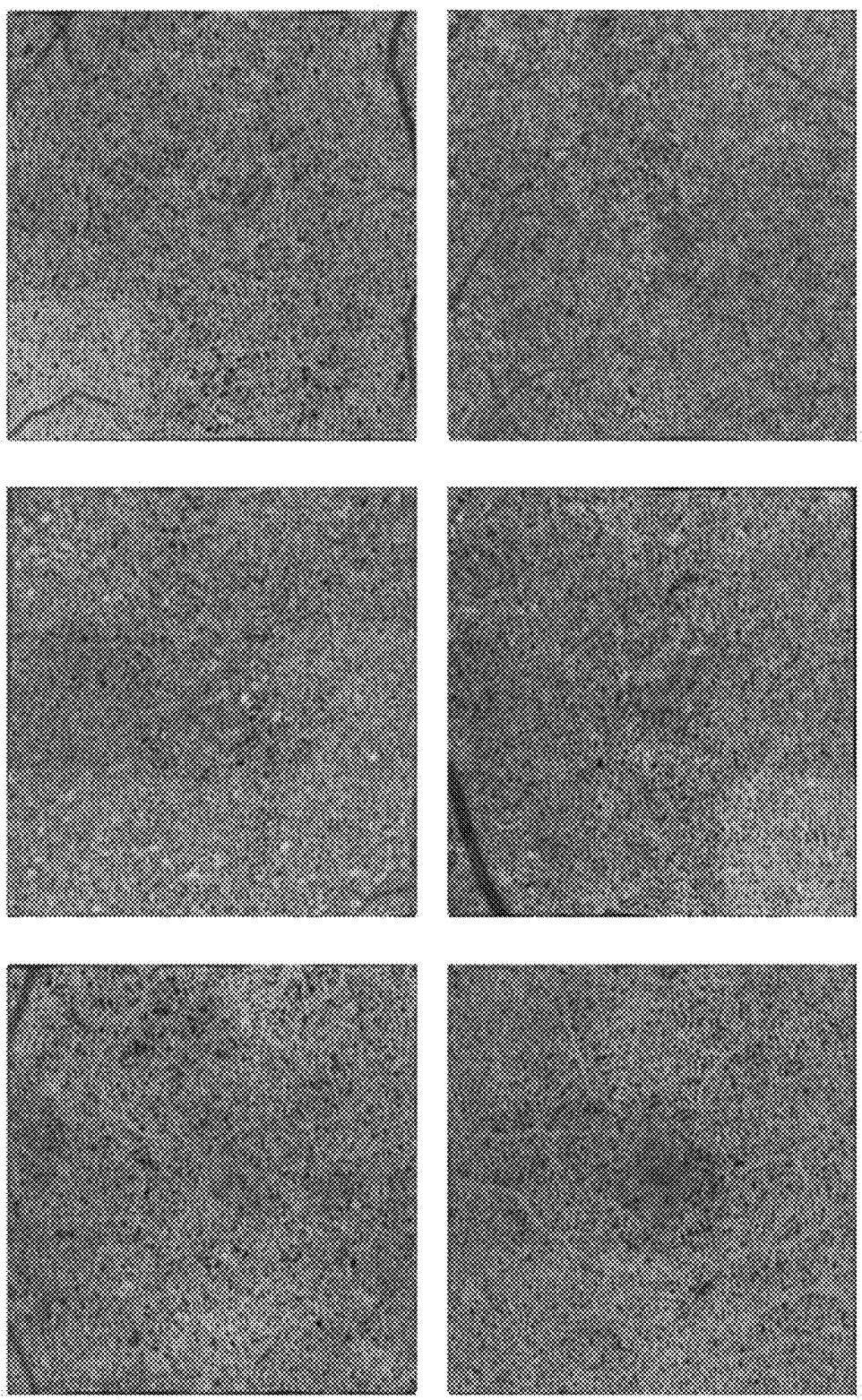
FIG. 9 are example images resulting from OCT angiography image averaging.

FIG. 9 comprises example images of the choriocapillaris resulting from OCT angiography image averaging. These images can have greater clarity and accuracy than OCT images that do not undergo the averaging and registration processes disclosed herein.

Figure 10:
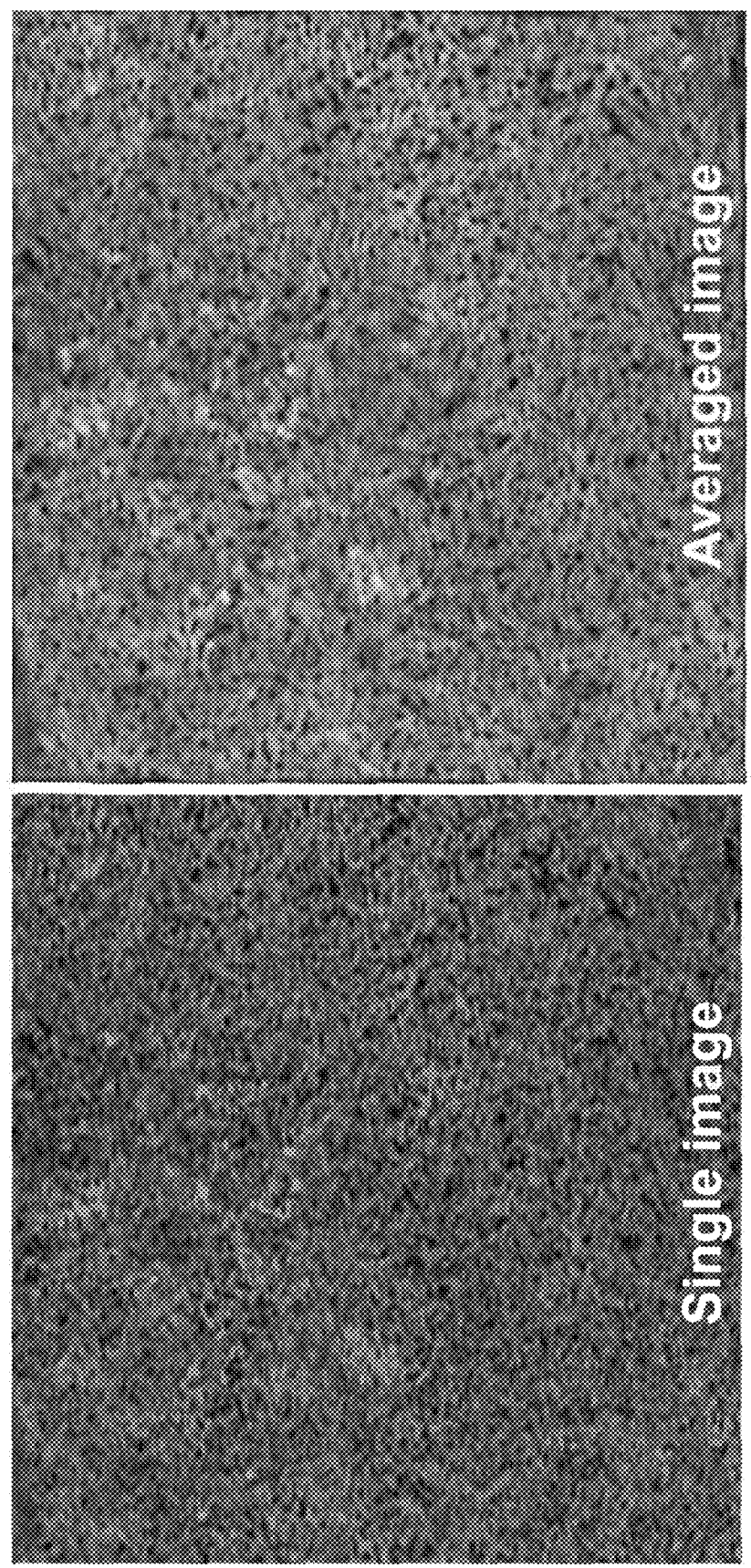
FIG. 10 illustrates example OCT images generated with and without OCT imaging angiography image averaging.

FIG. 10 illustrates example OCT images generated with and without OCT imaging angiography image averaging. FIG. 10A illustrates a single OCT image generated without OCT imaging angiography image averaging. FIG. 10B illustrates an averaged OCT image generated with OCT imaging angiography image averaging. FIGS. 10A and 10B illustrate the difference in the flow voids pattern between a single image and averaged image.

FIG. 11 comprises a table 1100 illustrating experimental data presenting differences in the flow voids size and number between FIGS. 10B and 10A, which were generated with and without OCT imaging angiography image averaging, respectively. As illustrated in table 1100, the number of flow voids is greater in the averaged image than in the single image. Furthermore, flow voids in the averaged image were smaller in averaged image than those in single image. Finally, small flow voids were depicted better in averaged image.

Figure 12:
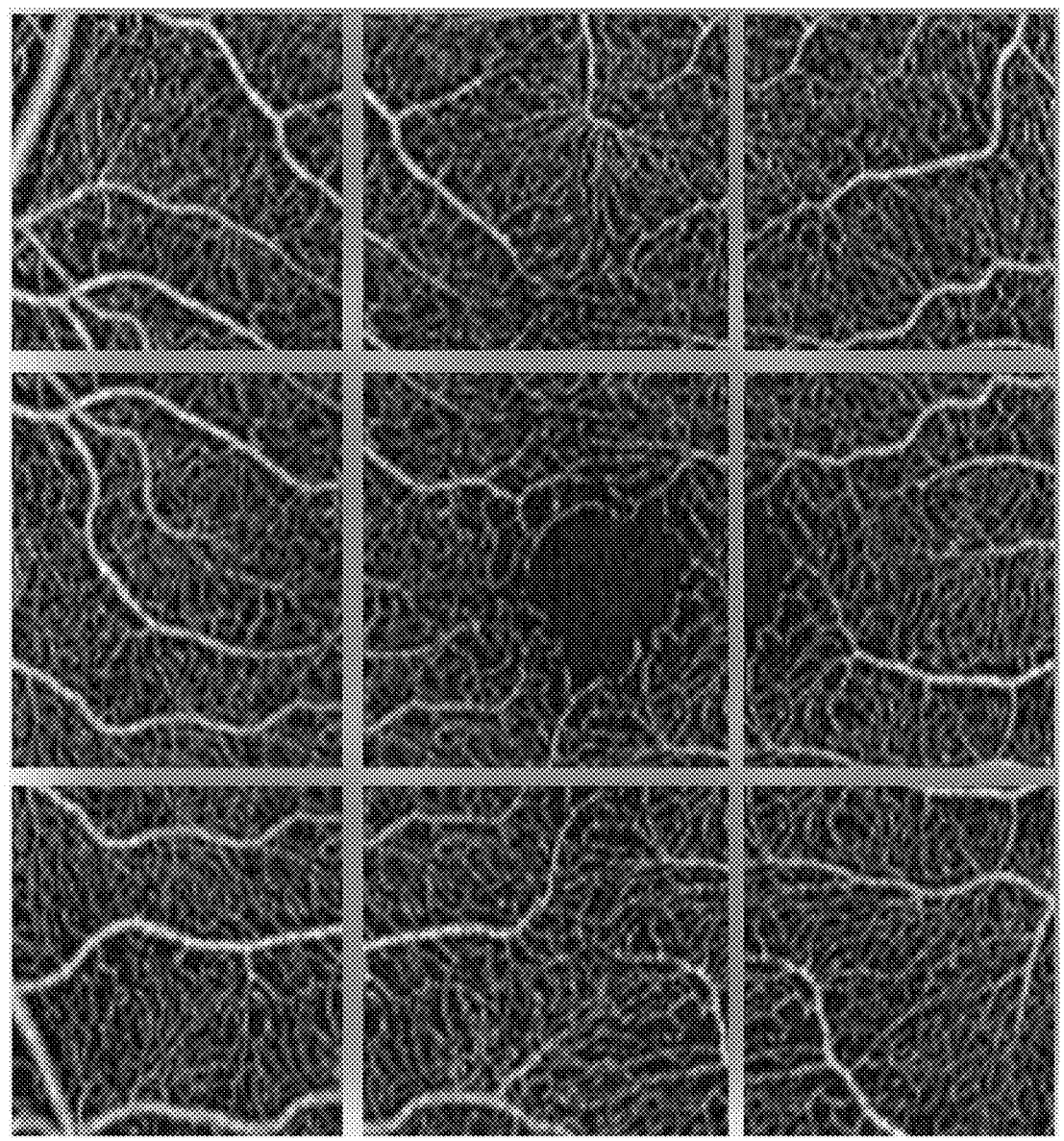
FIG. 12 illustrates an example image that has been sectored according to some embodiments of the sectoring systems, methods, and devices disclosed herein, which may occur prior to registration of each individual sector.

FIG. 12 illustrates an example image that has been sectored according an embodiment of a sectoring process disclosed herein.

In some embodiments, the enface images can be broken into smaller pieces or sectors prior to registration. In some embodiments, each of the image pieces or image sectors can undergo registration individually. In some embodiments, after each of the image pieces or image sectors undergo registration individually, the full enface image can be recompiled or stitched back together. In some embodiments, after individual processing and registration of the sector images, the sectors are put back into place to create a full resultant image. In some embodiments, this sectoring process may be necessary because of the precision required to obtain a detailed and accurate image of a structure. In some embodiments, this sectoring process may be necessary to obtain an accurate image alignment. In some embodiments, because the structure or layer being imaged requires a very high level of precision in the accuracy of a registration or alignment, the sectoring process may be completed to provide greater exactness. In some embodiments, sectoring the enface images and then applying one or more registration techniques to each sector or piece can result in better final image quality. In some embodiments, the sectoring process will prevent the final images from being flawed by subtle misalignments that may occur without sectoring.

In some embodiments, the deep layer to be aligned can be the choriocapillaris. Because the choriocapillaris comprises tightly spaced and small blood vessels, the accuracy and quality of OCT images of the choriocapillaris can be affected significantly by subtle shifts, including translational and rotational movement, during imaging. In some embodiments, to increase the quality of the final images, the system can sector enface images of the choriocapillaris, and then complete registration and alignment of each sector individually. In some embodiments, after registration and alignment of each sector, each sector can be recompiled to create a clear and complete image. In some embodiments, sectoring is necessary because of the nature of the vessel complex being imaged. In some embodiments, sectoring will increase the quality and accuracy of the overall image and provide a better alignment than could be obtained by applying registration techniques only to the complete enface image.

In some embodiments, each sector can comprise a square shape within the enface image, as illustrated in FIG. 12. However, in other embodiments, each sector can comprise a rectangle, circle, triangle, octagonal shape, or any other two-dimensional shape considered to be most appropriate or convenient. In some embodiments, each sector can have the same shape. In other embodiments, each sector can comprise a different shape or some sectors can have the same shape while other sectors have differing shapes.

In some embodiments, each sector can comprise a sector area of an enface image. In some embodiments, each sector can comprise a square shape having a sector area of about 1 mm with about 1 mm sides. In some embodiments, an enface image which comprises about a 3 mm by 3 mm square can be sectored into nine square sectors, each of which can have about 1 mm by 1 mm sides. In some embodiments, each sector can comprise a square shape having dimensions between about 0.3 mm by 0.3 mm to about 12.0 mm by 12.0 mm. For example, each sector can comprise a square shape having dimensions of about 0.3 mm by 0.3 mm, 0.4 mm by 0.4 mm, 0.5 mm by 0.5 mm, 0.6 mm by 0.6 mm, 0.7 mm by 0.7 mm, 0.8 mm by 0.8 mm, 0.9 mm by 0.9 mm, 1.0 mm by 1.0 mm, 1.5 mm by 1.5 mm, 2.0 mm by 2.0 mm, 2.5 mm by 2.5 mm, 3.0 mm by 3.0 mm, 3.5 mm by 3.5 mm, 4.0 mm by 4.0 mm, 4.5 mm by 4.5 mm, 5.0 mm by 5.0 mm, 5.5 mm by 5.5 mm, 6.0 mm by 6.0 mm, 6.5 mm by 6.5 mm, 7.0 mm by 7.0 mm, 7.5 mm by 7.5 mm, 8.0 mm by 8.0 mm, 8.5 mm by 8.5 mm, 9.0 mm by 9.0 mm, 9.5 mm by 9.5 mm, 10.0 mm by 10.0 mm, 10.5 mm by 10.5 mm, 11.0 mm by 11.0 mm, 11.5 mm by 11.5 mm, 12.0 mm by 12.00, and/or within any range between the aforementioned values.

In some embodiments, the size and/or shape of the sectors may be determined at least based on the processing power of a computer that is utilized to complete the sectoring and registration, the amount of available to process the images, and/or the amount of detail needed in the final images. In some embodiments, the sectoring and registration processes may be automated by a computer. In some embodiments, a computer may able to determine an optimal sector size and/or shape based on at least the size of an enface image, the clarity and accuracy of resultant processed images, and/or other empiric criteria. In some embodiments, the computer may test the processing and registration using a certain sector size and/or shape for a plurality of images, and then based on the clarity and accuracy of the resultant image, either accept the resultant image or re-sector and re-process the original image. In some embodiments, the computer can continuously test different sector sizes and/or shapes until a resultant image is obtained that meets a clarity and/or accuracy threshold.

In some embodiments, the computer may consider the resultant image clarity and/or accuracy based on any image characteristics, for example, sharpness of image features, edge sharpness, edge strength, fractal dimensions, vessel density, noise magnitude, brightness, contrast, contrast to noise ratio, and/or other objective or subjective criteria. In some embodiments, the computer may utilize tests of past images to select the initial sector sizes and/or shapes for a new set of OCT images, such that the processing time can be reduced as the computer finds optimal variables for producing clear and accurate resultant images.

In some embodiments, an initial alignment or registration can be completed using vessel features of entire non-sectored images of a superficial layer. After this initial registration, the image can then be sectored, and registration can be completed on each individual sector to increase the accuracy of the alignment. In some embodiments, the sectors are recompiled on a pixel-to-pixel basis.

Figure 13:
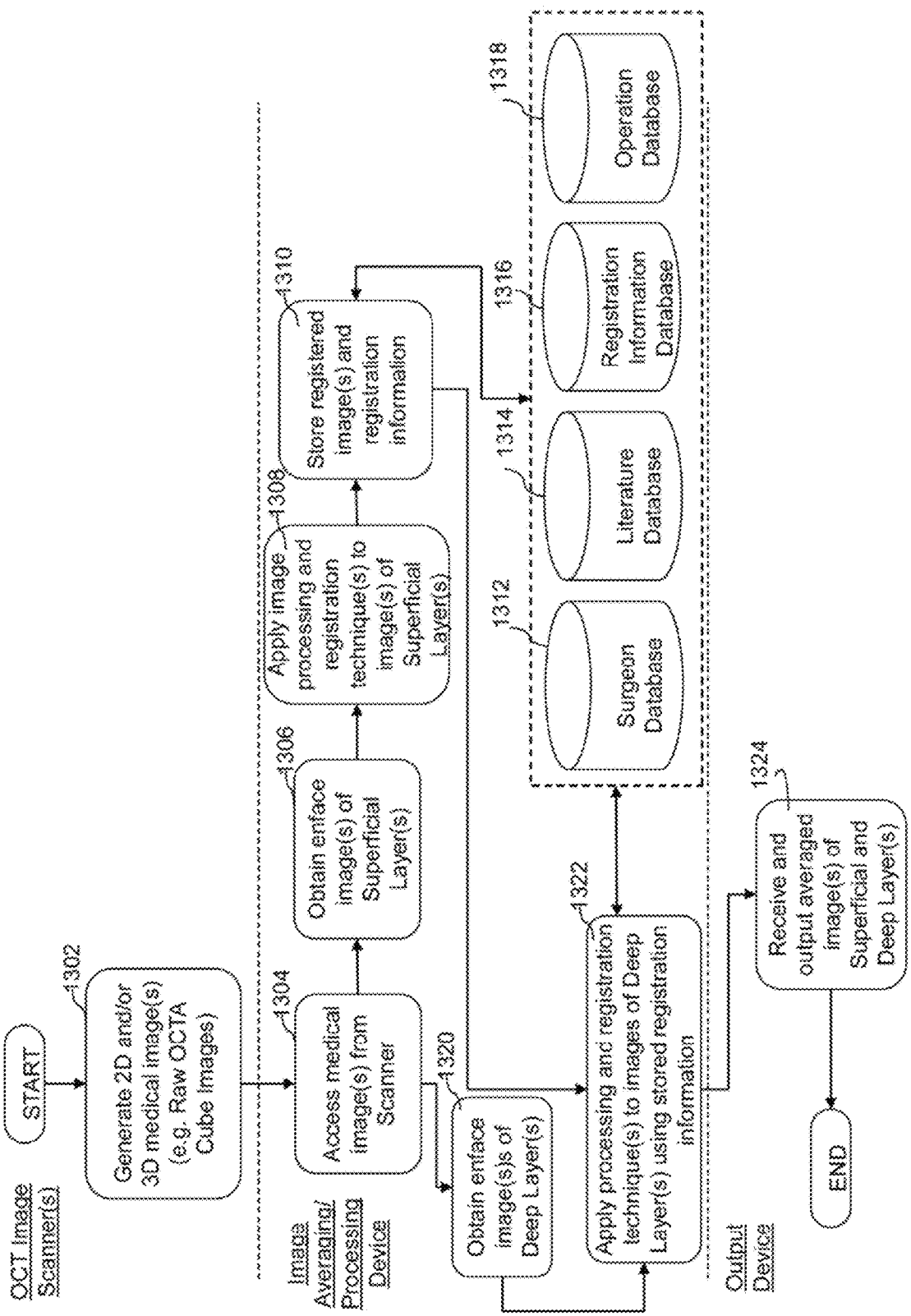
FIG. 13 illustrates a flowchart of an example embodiment of an OCT imaging method for obtaining and processing images of biological material.

FIG. 13 illustrates a flowchart of an example embodiment of an OCT imaging method for obtaining and processing images of biological material. In some embodiments, at 1302, one or more OCT image scanners generate 2D and/or 3D medical image(s), for example, raw OCTA cube images. In some embodiments, at 1304, an image averaging and processing device can access the medical image(s) from the scanner.

In some embodiments, at 1306, the image averaging and processing device can generate or obtain enface image(s) of one or more superficial layers. In other embodiments, the scanner can generate or create the enface image(s) of the superficial layers. In some embodiments, at 1308, the image averaging and processing device can apply image processing and registration technique(s) to image(s) of a superficial layer(s) of biological material to obtain registered images and registration information data. In some embodiments, at 1310, the registered image(s) and registration information can be stored in one or more databases, including, for example, a surgeon database 1312, a literature database 1314, a registration information database 1316, and/or an operation database 1318. In some embodiments, at 1320, the image averaging and processing device can generate or obtain enface image(s) of one or more deep layers. In other embodiments, the scanner can generate or create the enface image(s) of the deeper layers. In some embodiments, at 1322, the image averaging and processing device can apply processing and registration technique(s) to the enface images of the deep layer(s) using stored registration information from the one or more databases.

In some embodiments, the enface images may be sectored prior to registration, and then registration can be conducted on each sector individually, before recompiling the sectors into a complete registered image. In some embodiments, at 1324, an output device can receive the averaged images of the superficial and deep layers from the image averaging and processing device and can output the images.

Figure 14:
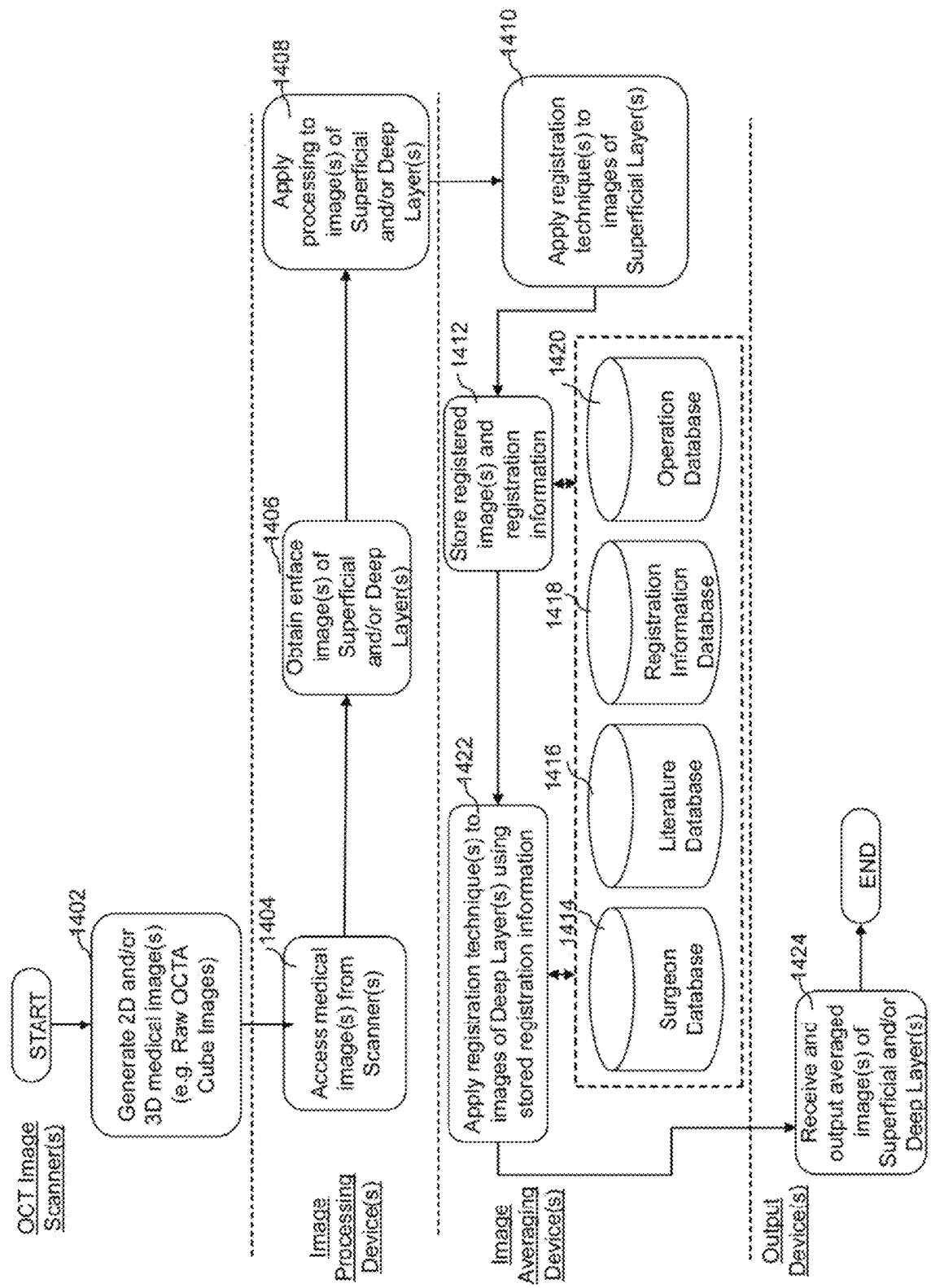
FIG. 14 illustrates a flowchart of another example embodiment of an OCT imaging method for obtaining and processing images of biological material.

FIG. 14 illustrates a flowchart of another example embodiment of an OCT imaging method for obtaining and processing images of biological material. In some embodiments, at 1402, one or more OCT image scanners generate 2D and/or 3D medical image(s), for example, raw OCTA cube images. In some embodiments, at 1404, an image processing device can access the medical image(s) from the scanner.

In some embodiments, at 1406, the image processing device can generate or obtain enface image(s) of one or more superficial layers and deep layers. In other embodiments, the scanner can generate or create the enface image(s) of the superficial layers and deep layer(s) of the biological material. In some embodiments, at 1408, the image processing device can apply image processing to image(s) of a superficial layer(s) and/or deep layer(s) of biological material to obtain processed images. In some embodiments, this processing can comprise sectoring, cropping, or other functions as discussed herein. In some embodiments, at 1410, an imaging averaging device can apply registration technique(s) to the processed images of superficial layer(s). In some embodiments, at 1412, the registered image(s) and registration information can be stored in one or more databases, including, for example, a surgeon database 1414, a literature database 1416, a registration information database 1418, and/or an operation database 1420. In some embodiments, at 1422, the image averaging device can apply registration technique(s) to the enface images of the deep layer(s) using stored registration information from the one or more databases.

In some embodiments, the enface images may be sectored prior to registration, and then registration can be conducted on each sector individually, before recompiling the sectors into a complete registered image.

In some embodiments, at 1424, an output device can receive the averaged images of the superficial and deep layers from the image averaging device and can output the images.

Figure 15:
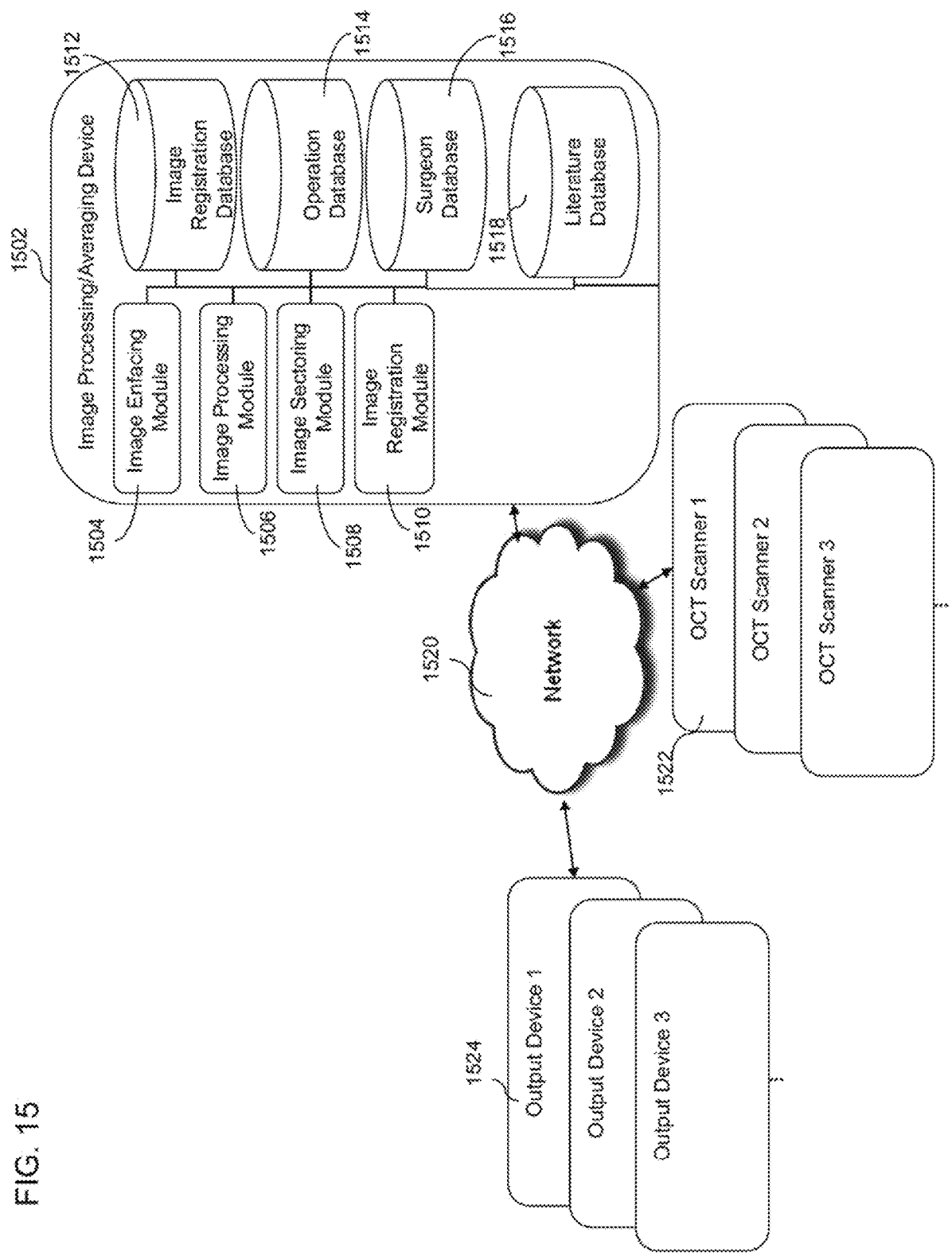
FIG. 15 illustrates a block diagram of an example embodiment of a computer system configured to run software for implementing one or more embodiments of the OCT imaging systems, methods, and devices for obtaining and processing images of biological material.

FIG. 15 illustrates a block diagram of an example embodiment of a computer system configured to run software for implementing one or more embodiments of the OCT imaging systems, methods, and devices for obtaining and processing images of biological material.

In some embodiments, an image processing/averaging device 1502 may be comprised of an image enfacing module 1504, an image processing module 1506, a sectoring module 1508, an image registration module 1510, an image registration database 1512, an operation database 1514, a surgeon database 1516, and/or a literature database 1518. The image processing/averaging device can be connected to a network 1520. The network can be configured to connect the image processing/averaging device to one or more OCT Scanners 1522 and one or more output devices 1524.

The image enfacing module 1504 may function by generating enface images from the raw OCT data provided, for example, from one of the OCT scanners 1522 through the network 1520. The image processing module 1506 may function by performing intermediate functions on the enface images, such as cropping, sectoring, averaging images at all parts of the process as discussed herein. The image sectoring module 1508 may function by performing sectoring enface images in preparation of individual registration of each sector within a plurality of enface images. The image registration module 1510 may function by performing linear, affine, and or elastic registration on the enface images or on individual sectors of the enface images. Each of the modules can be configured to interact with each other and the databases discussed herein.

The image registration database 1512 may provide a collection of registered images and registration information to be utilized in the systems and methods disclosed herein. The operation database 1514 may provide a collection of all surgical operations that have been performed utilizing the system and/or related data. The surgeon database 1516 may provide a collection of all surgeons who have utilized the system and/or related data, such as surgeon preferences, skill levels, or the like. The literature database 1518 may provide a collection of scientific literature related to OCT image registration and averaging.

Figure 16:
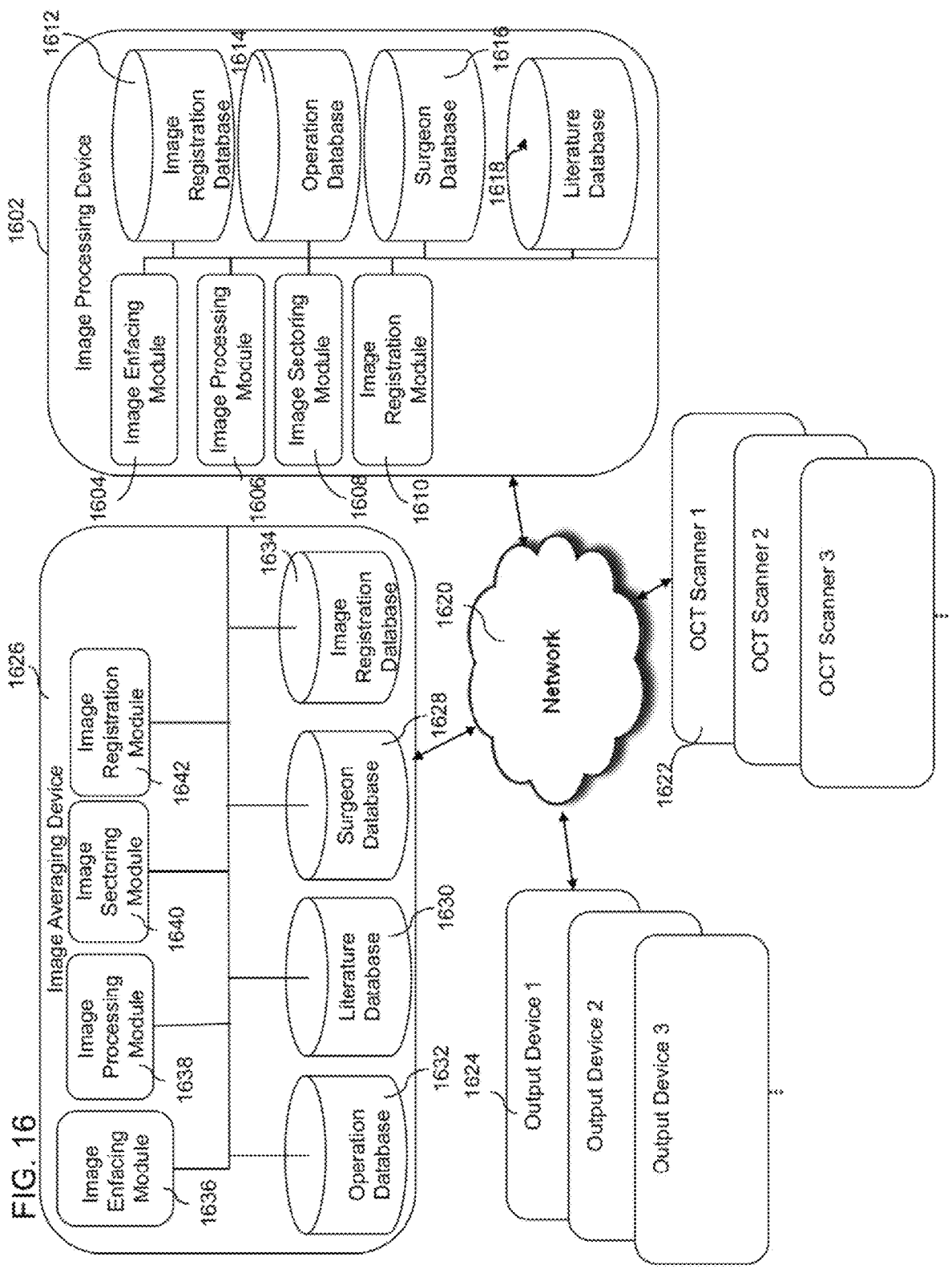
FIG. 16 illustrates a block diagram of another example embodiment of a computer system configured to run software for implementing one or more embodiments of the OCT imaging systems, methods, and devices for obtaining and processing images of biological material.

FIG. 16 illustrates a block diagram of another example embodiment of a computer system configured to run software for implementing one or more embodiments of the OCT imaging systems, methods, and devices for obtaining and processing images of biological material.

In some embodiments, an image processing device 1602 may be comprised of an image enfacing module 1604, an image processing module 1606, a sectoring module 1608, an image registration module 1610, an image registration database 1612, an operation database 1614, a surgeon database 1616, and/or a literature database 1618. The image processing device can be connected to a network 1620. The network can be configured to connect the image processing device to an imaging averaging device 1626, one or more OCT Scanners 1622 and one or more output devices 1624.

In some embodiments, an image averaging device 1626 may be comprised of an image enfacing module 1636, an image processing module 1638, a sectoring module 1640, an image registration module 1642, an image registration database 1634, an operation database 1632, a surgeon database 1628, and/or a literature database 1630. The image averaging device can be connected to a network 1620. The network can be configured to connect the image averaging device to an imaging processing device 1602, one or more OCT Scanners 1622 and one or more output devices 1624.

In some embodiments, the image processing device and the image averaging device can perform different portions of the methods discussed herein or comprise different parts of the systems described herein.

The image enfacing modules 1604, 1636 may function by generating enface images from the raw OCT data provided, for example, from one of the OCT scanners 1622 through the network 1620. The image processing modules 1606, 1638 may function by performing intermediate functions on the enface images, such as cropping, sectoring, averaging images at all parts of the process as discussed herein. The image sectoring modules 1608, 1640 may function by performing sectoring enface images in preparation of individual registration of each sector within a plurality of enface images. The image registration module 1610, 1642 may function by performing linear, affine, and or elastic registration on the enface images or on individual sectors of the enface images. Each of the modules can be configured to interact with each other and the databases discussed herein.

The image registration databases 1612, 1634 may provide a collection of registered images and registration information to be utilized in the systems and methods disclosed herein. The operation databases 1614, 1632 may provide a collection of all surgical operations that have been performed utilizing the system and/or related data. The surgeon databases 1616, 1628 may provide a collection of all surgeons who have utilized the system and/or related data, such as surgeon preferences, skill levels, or the like. The literature databases 1618, 1630 may provide a collection of scientific literature related to OCT image registration and averaging.

Figure 17:
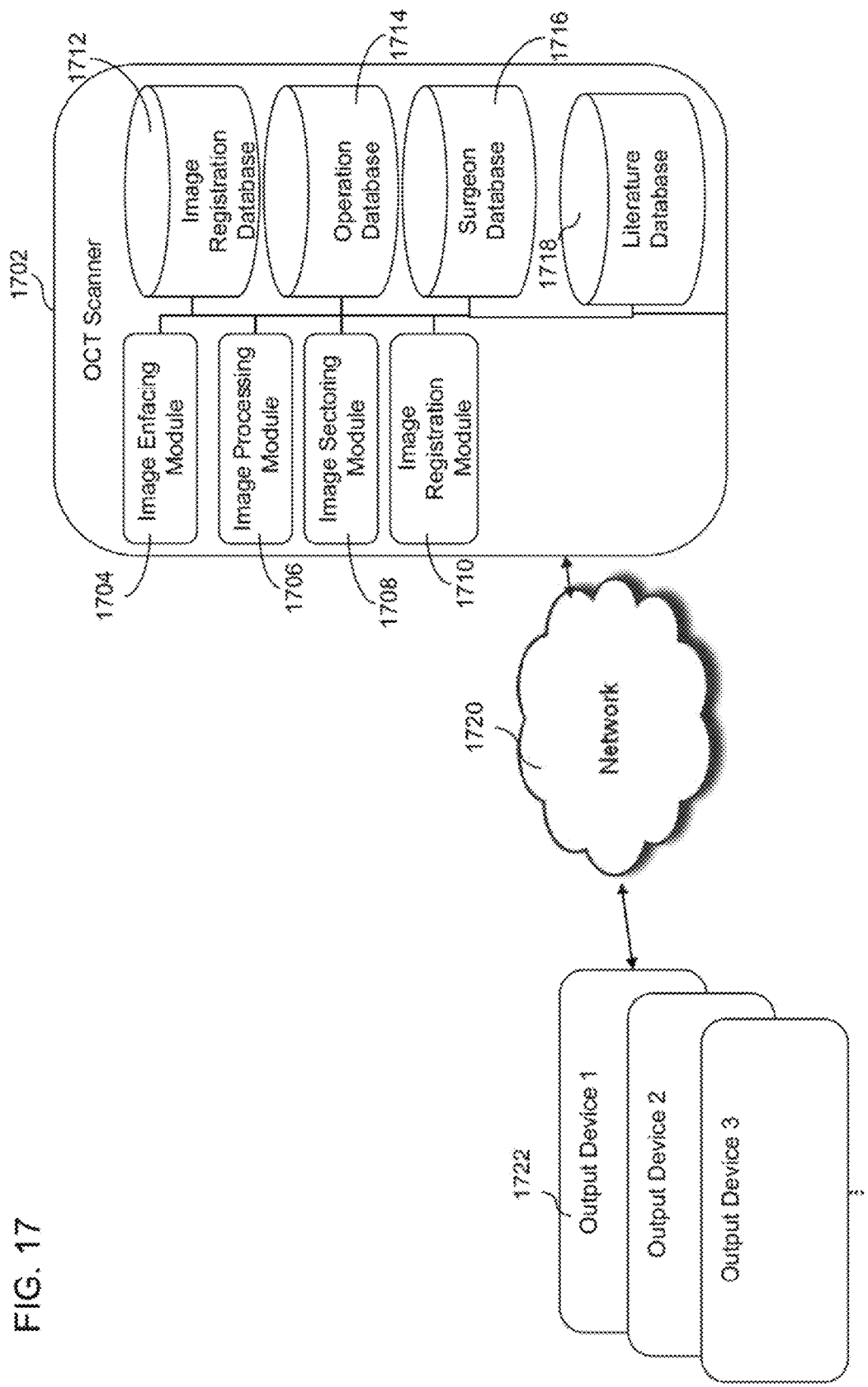
FIG. 17 illustrates a block diagram of another example embodiment of a computer system configured to run software for implementing one or more embodiments of the OCT imaging systems, methods, and devices for obtaining and processing images of biological material.

FIG. 17 illustrates a block diagram of another example embodiment of a computer system configured to run software for implementing one or more embodiments of the OCT imaging systems, methods, and devices for obtaining and processing images of biological material.

In some embodiments, an OCT Scanner 1702 may be comprised of an image enfacing module 1704, an image processing module 1706, a sectoring module 1708, an image registration module 1710, an image registration database 1712, an operation database 1714, a surgeon database 1716, and/or a literature database 1718. The image processing/averaging device can be connected to a network 1720. The network can be configured to connect the image processing/averaging device to one or more output devices 1722.

The image enfacing module 1704 may function by generating enface images from the raw OCT data generated by the OCT Scanner. The image processing module 1706 may function by performing intermediate functions on the enface images, such as cropping, sectoring, averaging images at all parts of the process as discussed herein. The image sectoring module 1708 may function by performing sectoring enface images in preparation of individual registration of each sector within a plurality of enface images. The image registration module 1710 may function by performing linear, affine, and or elastic registration on the enface images or on individual sectors of the enface images. Each of the modules can be configured to interact with each other and the databases discussed herein.

The image registration database 1712 may provide a collection of registered images and registration information to be utilized in the systems and methods disclosed herein. The operation database 1714 may provide a collection of all surgical operations that have been performed utilizing the system and/or related data. The surgeon database 1716 may provide a collection of all surgeons who have utilized the system and/or related data, such as surgeon preferences, skill levels, or the like. The literature database 1718 may provide a collection of scientific literature related to OCT image registration and averaging.

Figure 18:
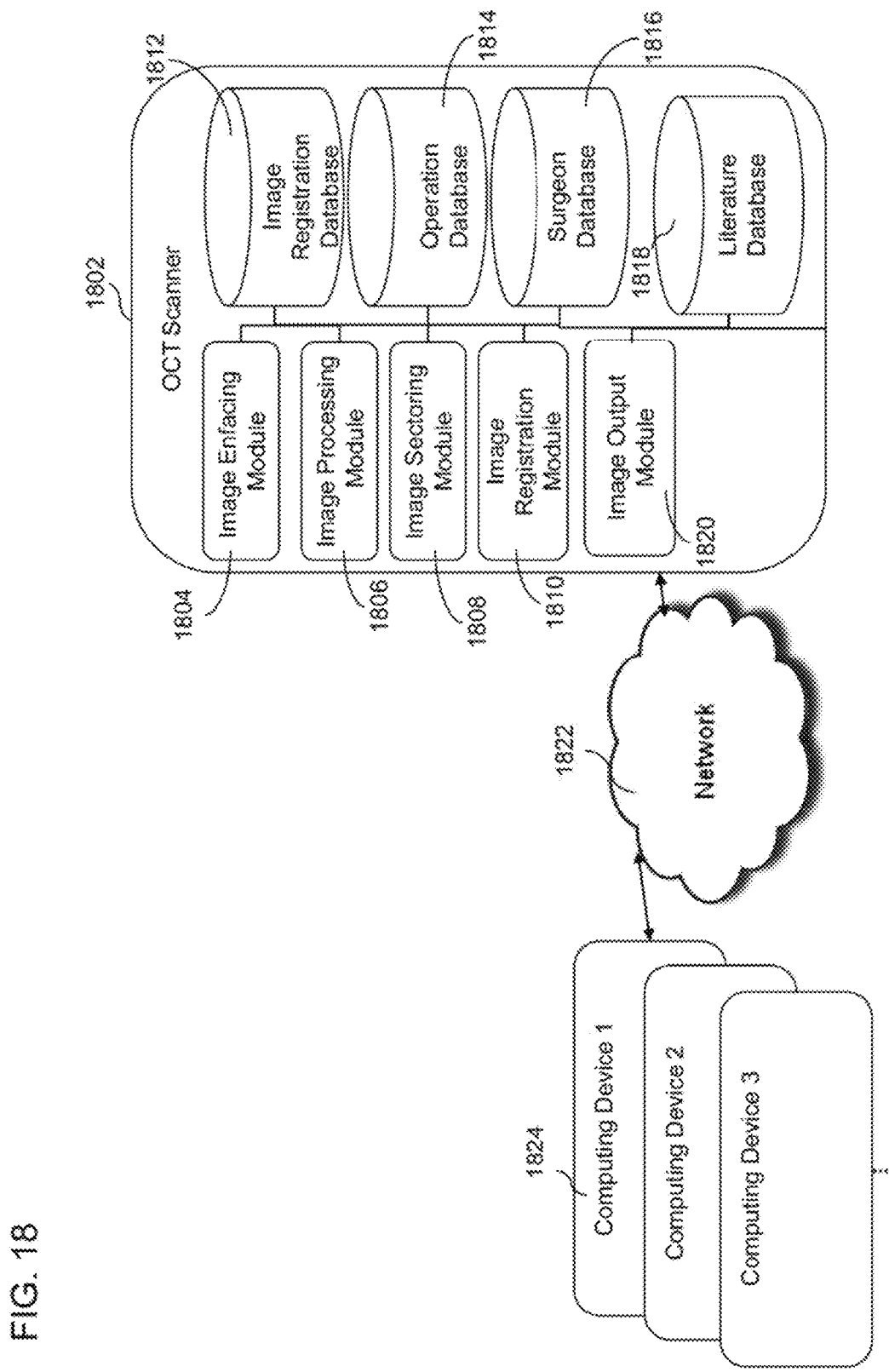
FIG. 18 illustrates a block diagram of another example embodiment of a computer system configured to run software for implementing one or more embodiments of the OCT imaging systems, methods, and devices for obtaining and processing images of biological material.

FIG. 18 illustrates a block diagram of another example embodiment of a computer system configured to run software for implementing one or more embodiments of the OCT imaging systems, methods, and devices for obtaining and processing images of biological material.

In some embodiments, an OCT Scanner 1802 may be comprised of an image enfacing module 1804, an image processing module 1806, a sectoring module 1808, an image registration module 1810, an image output module 1820, an image registration database 1812, an operation database 1814, a surgeon database 1816, and/or a literature database 1818. The image processing/averaging device can be connected to a network 1822. The network can be configured to connect the image processing/averaging device to one or more computing devices 1824, such as, for example, a tablet, mobile phone, personal computer, or cloud-based or physical servers.

The image enfacing module 1804 may function by generating enface images from the raw OCT data generated by the OCT Scanner. The image processing module 1806 may function by performing intermediate functions on the enface images, such as cropping, sectoring, averaging images at all parts of the process as discussed herein. The image sectoring module 1808 may function by performing sectoring enface images in preparation of individual registration of each sector within a plurality of enface images. The image registration module 1810 may function by performing linear, affine, and or elastic registration on the enface images or on individual sectors of the enface images. The image output module 1820 may function by outputting the complete averaged images to a user for viewing and/or analysis. Each of the modules can be configured to interact with each other and the databases discussed herein.

The image registration database 1812 may provide a collection of registered images and registration information to be utilized in the systems and methods disclosed herein. The operation database 1814 may provide a collection of all surgical operations that have been performed utilizing the system and/or related data. The surgeon database 1816 may provide a collection of all surgeons who have utilized the system and/or related data, such as surgeon preferences, skill levels, or the like. The literature database 1818 may provide a collection of scientific literature related to OCT image registration and averaging.

Computer System

Figure 19:
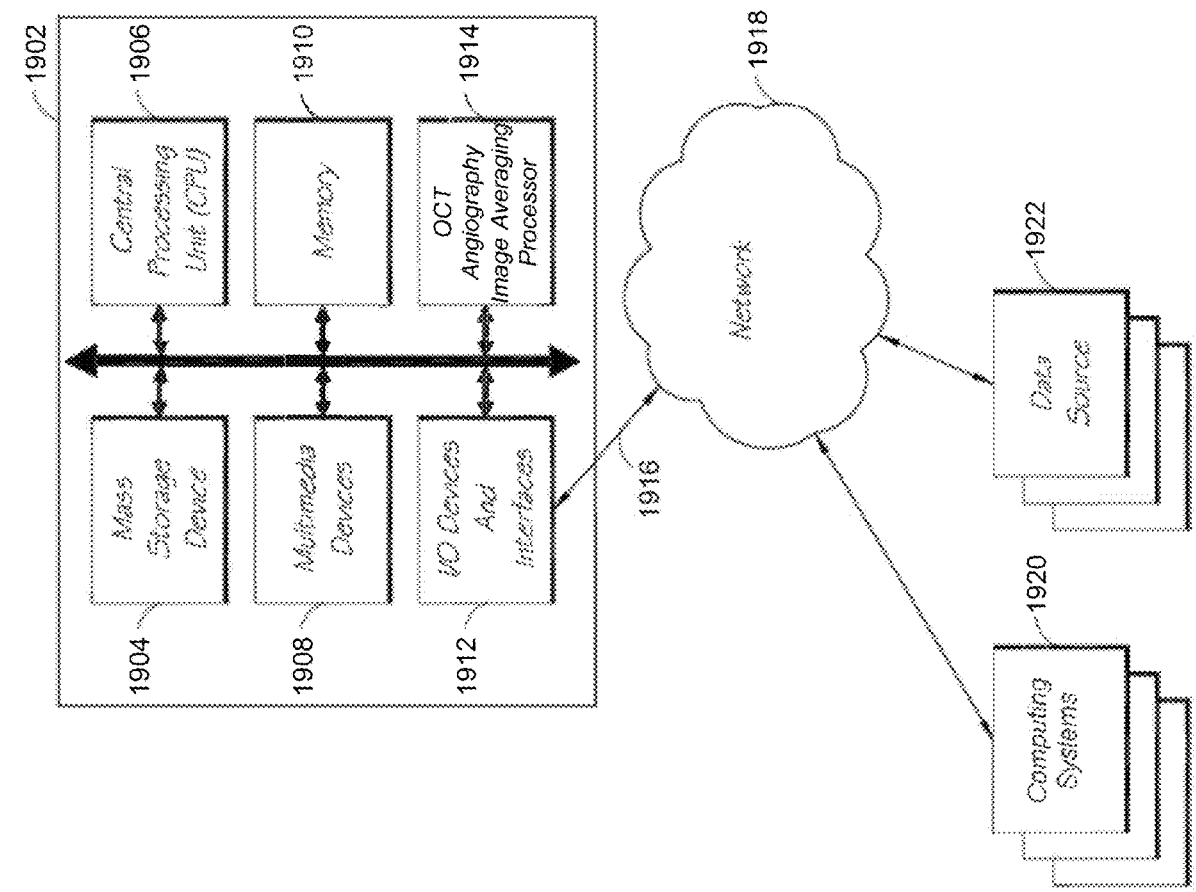
FIG. 19 is a block diagram depicting an example embodiment of a computer system configured to run software for implementing one or more embodiments of the OCT Angiography Image Averaging Processor systems, methods, and devices disclosed herein.

FIG. 19 is a block diagram depicting an embodiment of a computer hardware system configured to run software for implementing one or more embodiments of the OCT Angiography Image Averaging Processor systems, methods, and devices disclosed herein.

In some embodiments, the systems, processes, and methods described herein are implemented using a computing system, such as the one illustrated in FIG. 19. The example computer system 1902 is in communication with one or more computing systems 1920 and/or one or more data sources 1922 via one or more networks 1918. While FIG. 19 illustrates an embodiment of a computing system 1902, it is recognized that the functionality provided for in the components and modules of computer system 1902 may be combined into fewer components and modules, or further separated into additional components and modules.

The computer system 1902 can comprise an OCT Angiography Image Averaging Processor module 1914 that carries out the functions, methods, acts, and/or processes described herein. The OCT Angiography Image Averaging Processor module 1914 is executed on the computer system 1902 by a central processing unit 1906 discussed further below.

In general, the word "module," as used herein, refers to logic embodied in hardware or firmware or to a collection of software instructions, having entry and exit points. Modules are written in a program language, such as JAVA, C or C++, PYPHON or the like. Software modules may be compiled or linked into an executable program, installed in a dynamic link library, or may be written in an interpreted language such as BASIC, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems and may be stored on or within any suitable computer readable medium or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

The computer system 1902 includes one or more processing units (CPU) 1906, which may comprise a microprocessor. The computer system 1902 further includes a physical memory 1910, such as random access memory (RAM) for temporary storage of information, a read only memory (ROM) for permanent storage of information, and a mass storage device 1904, such as a backing store, hard drive, rotating magnetic disks, solid state disks (SSD), flash memory, phase-change memory (PCM), 3D XPoint memory, diskette, or optical media storage device. Alternatively, the mass storage device may be implemented in an array of servers. Typically, the components of the computer system 1902 are connected to the computer using a standards-based bus system. The bus system can be implemented using various protocols, such as Peripheral Component Interconnect (PCI), Micro Channel, SCSI, Industrial Standard Architecture (ISA) and Extended ISA (EISA) architectures.

The computer system 1902 includes one or more input/output (I/O) devices and interfaces 1912, such as a keyboard, mouse, touch pad, and printer. The I/O devices and interfaces 1912 can include one or more display devices, such as a monitor, that allows the visual presentation of data to a user. More particularly, a display device provides for the presentation of GUIs as application software data, and multi-media presentations, for example. The I/O devices and interfaces 1912 can also provide a communications interface to various external devices. The computer system 1902 may comprise one or more multi-media devices 1908, such as speakers, video cards, graphics accelerators, and microphones, for example.

The computer system 1902 may run on a variety of computing devices, such as a server, a Windows server, a Structure Query Language server, a Unix Server, a personal computer, a laptop computer, and so forth. In other embodiments, the computer system 1902 may run on a cluster computer system, a mainframe computer system and/or other computing system suitable for controlling and/or communicating with large databases, performing high volume transaction processing, and generating reports from large databases. The computing system 1902 is generally controlled and coordinated by an operating system software, such as z/OS, Windows, Linux, UNIX, BSD, SunOS, Solaris, MacOS, or other compatible operating systems, including proprietary operating systems. Operating systems control and schedule computer processes for execution, perform memory management, provide file system, networking, and I/O services, and provide a user interface, such as a graphical user interface (GUI), among other things.

The computer system 1902 illustrated in FIG. 19 is coupled to a network 1918, such as a LAN, WAN, or the Internet via a communication link 1916 (wired, wireless, or a combination thereof). Network 1918 communicates with various computing devices and/or other electronic devices. Network 1918 is communicating with one or more computing systems 1920 and one or more data sources 1922. The OCT Angiography Image Averaging Processor module 1914 may access or may be accessed by computing systems 1920 and/or data sources 1922 through a web-enabled user access point. Connections may be a direct physical connection, a virtual connection, and other connection type. The web-enabled user access point may comprise a browser module that uses text, graphics, audio, video, and other media to present data and to allow interaction with data via the network 1918.

Access to the OCT Angiography Image Averaging Processor module 1914 of the computer system 1902 by computing systems 1920 and/or by data sources 1922 may be through a web-enabled user access point such as the computing systems' 1920 or data source's 1922 personal computer, cellular phone, smartphone, laptop, tablet computer, e-reader device, audio player, or other device capable of connecting to the network 1918. Such a device may have a browser module that is implemented as a module that uses text, graphics, audio, video, and other media to present data and to allow interaction with data via the network 1918.

The output module may be implemented as a combination of an all-points addressable display such as a cathode ray tube (CRT), a liquid crystal display (LCD), a plasma display, or other types and/or combinations of displays. The output module may be implemented to communicate with input devices 1912 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 1902 may comprise a physical or logical connection established between a remote microprocessor and a mainframe host computer for the express purpose of uploading, downloading, or viewing interactive data and databases on-line in real time. The remote microprocessor may be operated by an entity operating the computer system 1902, including the client server systems or the main server system, an/or may be operated by one or more of the data sources 1922 and/or one or more of the computing systems 1920. In some embodiments, terminal emulation software may be used on the microprocessor for participating in the micro-mainframe link.

In some embodiments, computing systems 1920 who are internal to an entity operating the computer system 1902 may access the OCT Angiography Image Averaging Processor module 1914 internally as an application or process run by the CPU 1906.

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

The computing system 1902 may include one or more internal and/or external data sources (for example, data sources 1922). In some embodiments, one or more of the data repositories and the data sources described above may be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 1902 may also access one or more databases 1922. The databases 1922 may be stored in a database or data repository. The computer system 1902 may access the one or more databases 1922 through a network 1918 or may directly access the database or data repository through I/O devices and interfaces 1912. The data repository storing the one or more databases 1922 may reside within the computer system 1902.

Although the embodiments discussed herein generally relate to OCT imaging of ocular tissue, the systems, methods, and devices disclosed herein can be used for any 3-dimensional data sets of any biological or other material. For example, the systems, methods, and devices disclosed herein can be used with MRI, CT, or any other imaging systems or devices that produce 3-dimensional image or video data.

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present.

What is claimed is:

1. A system for processing images of a biological material, the system comprising:
   one or more computer readable storage devices configured to store a plurality of computer executable instructions; and
   one or more hardware computer processors in communication with the one or more computer readable storage devices and configured to execute the plurality of computer executable instructions in order to cause the system to:
      access, from one or more databases, one or more optical coherence tomography (OCT) images;
      generate, from the one or more OCT images, one or more first OCT images corresponding to a first tissue layer and one or more second OCT images corresponding to a second tissue layer;
      perform one or more image registration techniques on the one or more first OCT images to obtain image alignment data;
      align the one or more second OCT images using the obtained image alignment data; and
      generate an averaged OCT image of the second tissue layer from the one or more aligned second OCT images.

2. The system of claim 1, wherein the biological material comprises retinal, choroid, or another eye tissue.

3. The system of claim 2, wherein the another eye tissue is one of posterior eye wall tissue and anterior eye wall tissue.

4. The system of claim 2, wherein the first tissue layer and the second tissue layer comprise layers from a retinal vascular network.

5. The system of claim 4 wherein the retinal vascular network is a superficial vascular plexus.

6. The system of claim 1, wherein the one or more first OCT images or one or more second OCT images are generated using one of spectral domain OCT, swept source OCT, and another type of three-dimensional-imaging OCT.

7. The system of claim 1, wherein the one or more image registration techniques comprise linear registration techniques.

8. The system of claim 1, wherein the one or more image registration techniques comprise affine registration techniques.

9. The system of claim 1, wherein the one or more image registration techniques comprise elastic registration techniques.

10. The system of claim 1, wherein the system is configured to account for movement of the biological material during generation of the one or more first OCT images or one or more second OCT images.

11. The system of claim 10, wherein the movement comprises at least one of translational movement and rotational movement.

12. The system of claim 1, wherein the first tissue layer comprises well-defined features or landmarks.

13. The system of claim 12, wherein the well-defined features or landmarks comprise blood vessels.

14. The system of claim 1, wherein the first tissue layer comprises a superficial tissue layer.

15. The system of claim 14, wherein the second tissue layer comprises a deep tissue layer.

16. A method for processing images of a biological material, the method comprising:
   accessing one or more optical coherence tomography (OCT) images;
   generating, from the one or more OCT images, one or more first OCT images corresponding to a first tissue layer and one or more second OCT images corresponding to a second tissue layer;
   performing one or more image registration techniques on the one or more first OCT images to obtain image alignment data;
   aligning the one or more second OCT images using the obtained image alignment data; and
   generating an averaged OCT image of the second tissue layer from the one or more aligned second OCT images.

17. The method of claim 16, wherein the biological material comprises retinal, choroid, or another eye tissue.

18. The method of claim 16, wherein the second tissue layer comprises a choriocapillaris or deep capillary plexus.

19. The method of claim 16, wherein the first tissue layer comprises a superficial vascular plexus.

20. The method of claim 16, wherein the one or more image registration techniques comprise linear registration techniques.

* * * * *